(12) United States Patent
Ritter et al.

(10) Patent No.: US 8,609,901 B2
(45) Date of Patent: Dec. 17, 2013

(54) HIGHLY SELECTIVE PROCESS FOR PRODUCING ORGANODIPHOSPHITES

(75) Inventors: Joachim C. Ritter, Wilmington, DE (US); Thomas E. Vos, Beaumont, TX (US)

(73) Assignee: Invista North America S.A R.L., Wilmington, DE (US)

( * ) Notice: Subject to any disclaimer, the term of this patent is extended or adjusted under 35 U.S.C. 154(b) by 667 days.

(21) Appl. No.: 12/760,814

(22) Filed: Apr. 15, 2010

(65) Prior Publication Data

US 2010/0267990 A1    Oct. 21, 2010

Related U.S. Application Data

(60) Provisional application No. 61/171,290, filed on Apr. 21, 2009, provisional application No. 61/171,295, filed on Apr. 21, 2009.

(51) Int. Cl.
*C07F 9/06* (2006.01)

(52) U.S. Cl.
USPC ............... 568/14; 568/10; 568/11; 568/12

(58) Field of Classification Search
USPC ..................... 568/10, 11, 12, 14
See application file for complete search history.

(56) References Cited

U.S. PATENT DOCUMENTS

| | | |
|---|---|---|
| 3,037,052 A | 5/1962 | Bortnick |
| 5,235,113 A | 8/1993 | Sato |
| 5,512,696 A | 4/1996 | Kreutzer et al. |
| 5,821,378 A | 10/1998 | Foo |
| 6,069,267 A * | 5/2000 | Tam ........................... 558/95 |
| 6,175,043 B1 | 1/2001 | Bunel |
| 2003/0100802 A1 | 5/2003 | Shapiro |

FOREIGN PATENT DOCUMENTS

| | | |
|---|---|---|
| WO | WO96/22968 | 8/1996 |
| WO | WO97/33854 | 9/1997 |
| WO | WO9906356 | 2/1999 |
| WO | WO01/21580 | 3/2001 |
| WO | WO03/045552 | 6/2003 |
| WO | WO2004/050588 | 6/2004 |
| WO | WO2004/091780 | 10/2004 |
| WO | WO2007/109005 | 9/2007 |

OTHER PUBLICATIONS

Tetrahedron Letters, 1994, 35, 7983-7984.

* cited by examiner

*Primary Examiner* — Johann R Richter
*Assistant Examiner* — Pancham Bakshi
(74) *Attorney, Agent, or Firm* — Robert B. Furr, Jr.

(57) ABSTRACT

Disclosed is a method for making a diphosphite of Structure I, $$R^1-O\underset{R^2-O}{\overset{}{>}}P-O-Q-O-P\underset{O-R^2}{\overset{O-R^1}{<}}$$

Structure I

14 Claims, No Drawings

HIGHLY SELECTIVE PROCESS FOR PRODUCING ORGANODIPHOSPHITES

CROSS-REFERENCE TO RELATED APPLICATIONS

This application claims priority from U.S. Provisional Application Ser. Nos. 61/171,290 filed on Apr. 21, 2009 and 61/171,295 filed on Apr. 21, 2009.

FIELD OF THE INVENTION

The invention relates to a process for the synthesis of organodiphosphites.

BACKGROUND OF THE INVENTION

A key intermediate in the production of nylon is adiponitrile (ADN). ADN is commercially produced via hydrocyanation of 1,3-butadiene and 3-pentenenitrile (3PN) in the presence of a catalyst comprising nickel(0) and phosphite ligand. The phosphite ligand used commercially is a monodentate phosphite, such as a triarylphosphite, that forms nickel-ligand complexes serving as catalyst precursors for the reactions. Although useful, monodentate phosphites can result in relatively low catalyst activity and relatively high nickel consumption.

Recently, significant improvements in nickel catalyst activity and yield to 3PN and ADN have been realized by using catalysts comprising nickel(0) and bidentate phosphites as ligands. Bidentate phosphite ligands, in general, contain two phosphorus donor atoms that may form cyclic chelate structures with a single transition metal.

Bidentate phosphites, also referred to as diphosphites in this specification, of the general structure $(RO)_2P(OZO)P(OR)_2$ are of special interest. Traditionally, such diphosphites may be synthesized by a first reaction for preparing a phosphorochloridite, $(RO)_2PCl$, from the reaction of $PCl_3$ with ROH in the presence of a tertiary organic amine. Then in a subsequent reaction, a difunctional alcohol, such as HO—Z—OH, may react with the phosphorochloridite in the presence of additional tertiary organic amine to produce $(RO)_2P(OZO)P(OR)_2$. A function of the tertiary organic amine is to neutralize the HCl co-product in both reaction steps through the formation of a tertiary organic amine hydrogen chloride salt. The nature of ROH and HO—Z—OH as well as the conditions chosen for each reaction step may influence the selectivity to desired products, $(RO)_2PCl$ and $(RO)_2P(OZO)P(OR)_2$.

U.S. Pat. No. 5,235,113 and WO 96/22968, for example, disclose the synthesis of diphosphites. U.S. Pat. No. 5,235,113 discloses a process for the preparation of a diphosphite of structure $(RO)_2P(OAO)P(OR)_2$ where A is biphenyl and R is 3,6-di-t-butyl-2-naphthyl. WO 96/22968 discloses syntheses of multidentate phosphite compounds of the type $(ArO)_2P(OZO)P(OAr)_2$ where Ar and Z are substituted or unsubstituted aryl groups.

U.S. Pat. No. 6,069,267 provides a process for the preparation of organodiphosphites of the general formula $(R^1O)_2P(OZO)P(OR^1)_2$ wherein $R^1$ and Z are different substituted or unsubstituted aryl groups WO 2004/050588 discloses that low temperature and viscosity of the product mixture below 0° C., for example between 0° C. and −20° C., add significantly to operating cost and process complexity.

WO 2004/091780 also describes a process for preparing a crude ligand mixture comprising bidentate phosphite ligands of the structural formula $(R^1O)_2P(OZO)P(OR^1)_2$ by contacting a first reaction product, comprising $(R^1O)PCl$, at a temperature between about −25° C. and about +35° C. with about one half molar equivalent of HO—Z—OH in the presence of an organic base.

Accordingly, there is a need for a simple and selective process for preparing diphosphites that overcome problems identified in these references.

SUMMARY OF THE INVENTION

The present invention provides a method for producing a diphosphite of Structure I,

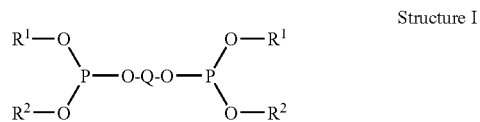

Structure I comprising the steps of:
contacting a phosphorochloridite of Structure II,

Structure II with a bisaryl compound selected from the group consisting of Structure III, Structure IV, and Structure V,

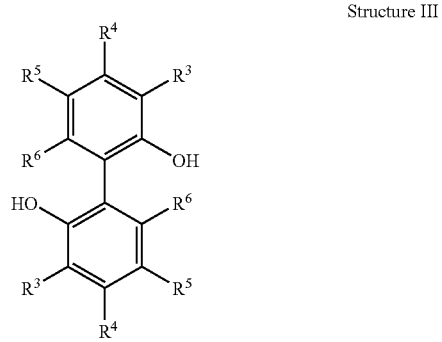

Structure III

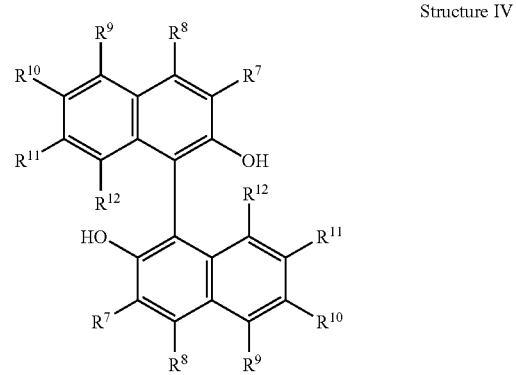

Structure IV

-continued

Structure V

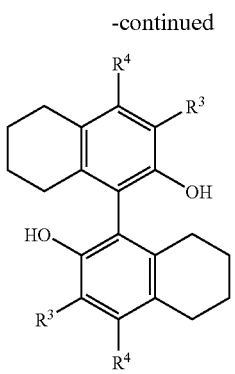

and a tertiary organic amine, comprising a basic nitrogen atom or a plurality of nitrogen atoms, to produce a reaction mixture comprising a diphosphite of Structure I;
wherein,
  the contacting is done by at least one contacting method selected from the group consisting of,
    (i). feeding the bisaryl compound to a mixture of phosphorochloridite and tertiary organic amine, and
    (ii). feeding the bisaryl compound and the tertiary organic amine either separately or as a mixture to the phosphorochloridite;
  and the contacting is done by controlling the feeding such that:
    a first mole ratio is at least 2.0 during all stages of the contacting, wherein the first mole ratio is defined as moles of phosphorochloridite in the reaction mixture divided by moles of bisaryl compound fed to the reaction mixture, and
    a second mole ratio is at least 1.0 during all stages of the contacting, wherein the second mole ratio is defined as moles of basic nitrogen atoms from the tertiary organic amine fed to the reaction mixture divided by moles of phosphorochloridite in the reaction mixture;
  and the method is characterized in that the contacting occurs at a temperature from about 10° C. to about 110° C. to produce the diphosphite in the reaction mixture with a selectivity between 70% and 100% from the bisaryl compound;
wherein,
  the selectivity equals moles of diphosphite produced in the reaction mixture divided by total moles of the bisaryl compound contacting the phosphorochloridite;
and wherein in Structures I to V,
  $R^1$ and $R^2$ are the same or different, substituted or unsubstituted, monovalent aryl groups; each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogenyl groups; and O-Q-O is a dianion of the bisaryl compound.

The reaction mixture may further comprise at least one aromatic hydrocarbon solvent.

The method can include controlling the feed such that the first mole ratio is between 2.1 to 2.7 during the stage of the contacting wherein phosphorochloridite conversion is between 90% and 100%. The phosphorochloridite conversion in this aspect and subsequent aspects is defined as 100% multiplied by a total moles of phosphorochloridite in the reaction mixture at the stage of the contacting divided by a total moles of phosphorochloridite undergoing the contacting by the method.

The feed can be controlled such that a phosphorochloridite concentration is greater than or equal to 0.02 moles per liter in the reaction mixture during the stage of the contacting wherein phosphorochloridite conversion is from 0% to 90%. For example, during the stage of the contacting wherein phosphorochloridite conversion is from 0% to 90%, the feeding is controlled such that a phosphorochloridite concentration in the reaction mixture is greater than or equal to 0.03 moles per liter, for example is greater than or equal to 0.04 moles per liter, for example is greater than or equal to 0.05 moles per liter.

The phosphorochloridite concentration can be between 0.02 and 2.0 moles per liter in the reaction mixture during the stage of the contacting wherein phosphorochloridite conversion is from 0% to 90%.

The method can include controlling the second mole ratio from 1.0 to 1.5 during any stage of the contacting.

The method can include feeding the bisaryl compound to the phosphorochloridite at a feed rate between 0.04 and 10 molar equivalents per hour, relative to total moles of phosphorochloridite undergoing the contacting by the method.

The bisaryl compound can be fed to the phosphorochloridite as a bisaryl solution comprising the bisaryl compound and hydrocarbon solvent.

The reaction mixture can be mixed, for example, stirred. If the reaction mixture further comprises an upper liquid surface, the contacting step can further comprises providing a stirring shaft comprising at least one impeller attached to the stirring shaft wherein at least one impeller is located below the upper liquid surface, and the feeding further comprises providing rotational energy to the stirring shaft to mechanically stir the reaction mixture.

The method may further comprising feeding the bisaryl solution to the phosphorochloridite by at least one mixing method selected from the group consisting of, feeding the bisaryl compound to the reaction mixture above the upper liquid surface by flowing the bisaryl solution through at least one liquid distributor that disperses the bisaryl solution over at least a portion of the upper liquid surface;

feeding the bisaryl compound to the reaction mixture above the upper liquid surface by flowing the bisaryl solution through at least one liquid distributor that disperses the bisaryl solution over at least a portion of the upper surface and feeding the tertiary organic amine to the reaction mixture below the upper liquid surface;

feeding the bisaryl compound to the reaction mixture by flowing the bisaryl solution through at least one feed line that directs the bisaryl solution toward an impeller located below the upper liquid surface;

feeding the bisaryl compound to the reaction mixture by flowing the bisaryl solution through at least one feed line that directs the bisaryl solution toward an impeller located below the upper liquid surface and feeding the tertiary organic amine to the reaction mixture by flowing the tertiary organic amine through at least one feed line that directs the tertiary organic amine toward an impeller located below the upper liquid surface; and the bisaryl solution further comprises at least a portion of the tertiary organic amine fed to the reaction mixture and feeding the bisaryl compound to the reaction mixture by flowing the bisaryl solution, further comprising the tertiary organic amine, through at least one feed line that directs the bisaryl solution toward an impeller located below the upper liquid surface.

The method may include limiting the amount of water present in the reaction mixture. For example, the bisaryl compound, the tertiary organic amine, or a combination of the bisaryl compound and the tertiary organic amine, contact the phosphorochloridite to provide a reaction mixture containing a total of from 0 ppm to 300 ppm by weight of water.

The method may include precipitating a tertiary organic amine hydrogen chloride salt from the reaction mixture during the contacting step.

The method may further include producing at least one phosphorus-containing co-product in the reaction mixture selected from the group consisting of $P(OR^1)(OR^2)_2$, $P(OR^1)_2(OR^2)$, $P(OR^1)_3$, $P(OR^2)_3$, a compound of Structure VIIa, and a compound of Structure VIIb,

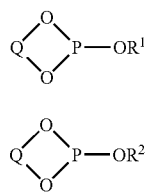

Structure VIIa

Structure VIIb wherein, less than 30% of the total phosphorus in the reaction mixture is in the form of the at least one phosphorus-containing co-product produced from the contacting.

DETAILED DESCRIPTION OF THE INVENTION

The disclosed method relates to a simple and highly selective process for producing bidentate diphosphites of Structure I comprising the steps of contacting a phosphorochloridite of Structure II with a bisaryl compound selected from the group consisting of Structure III, Structure IV, and Structure V, and a tertiary organic amine, comprising a basic nitrogen atom or a plurality of nitrogen atoms, to produce a reaction mixture comprising a diphosphite of Structure I. Scheme I shows a generalized reaction scheme for the process, including a monophosphite intermediate of Structure VI and monodentate triorganophosphite co-products, both cyclic and acyclic, of Structures VII and VIII, respectively. In the Structures herein, $R^1$ and $R^2$ are the same or different, substituted or unsubstituted, monovalent aryl groups, for example, substituted or unsubstituted phenyl, naphthyl, anthracenyl, and phenanthrenyl groups. The bisaryl compound HO-Q-OH may have the following structures,

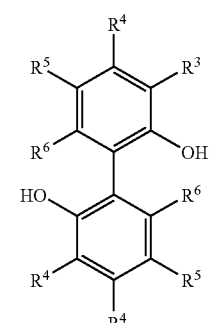

Structure III

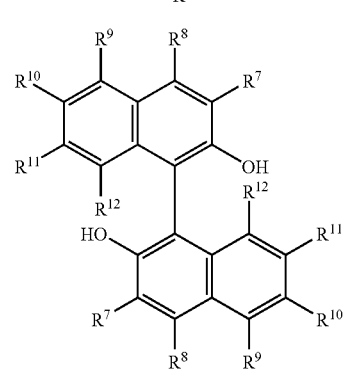

Structure IV

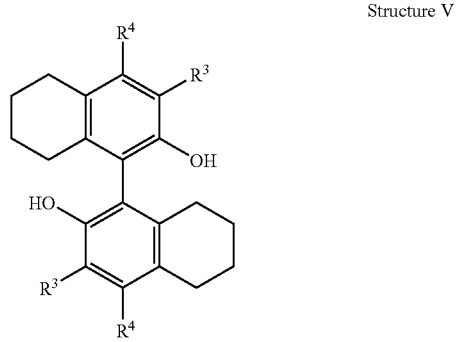

Structure V wherein each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogenyl groups; and O-Q-O is a dianion of the bisaryl compound. For example, linear, branched, and cyclic $C_1$ to $C_{18}$ alkyl; substituted or unsubstituted $C_6$ to $C_{18}$ aryl; substituted or unsubstituted $C_6$ to $C_{18}$ aryloxy; linear, branched, and cyclic $C_1$ to $C_{18}$ alkyloxy; linear and branched $C_2$ to $C_{18}$ alkoxyalkyl; substituted or unsubstituted $C_3$ to $C_{18}$ cyclic acetals; substituted or unsubstituted $C_7$ to $C_{18}$ carboaryloxy; linear, branched, and cyclic $C_2$ to $C_{18}$ carboalkoxy; substituted or unsubstituted $C_7$ to $C_{18}$ arylcarbonyl; and substituted or unsubstituted $C_2$ to $C_{18}$ alkylcarbonyl.

In the first step of the generalized reaction scheme, one equivalent of the phosphorochloridite (Structure II) reacts with a bisaryl compound HO-Q-OH (an abbreviated form of Structures III, IV, and V) to give a monophosphite intermediate (Structure VI). A suitable tertiary organic amine, comprising a basic nitrogen atom or a plurality of nitrogen atoms, such as a triorganoamine or a tertiary aromatic amine, is present to neutralize the acid (HCl) formed from the reaction of the phosphorochloridite with the bisaryl compound. The monophosphite intermediate (Structure VI) can then either react intermolecularly with one more equivalent of phosphorochloridite to give the desired diphosphite (Structure I), or it can react intramolecularly to produce the cyclic triorganophosphite co-product of Structure VII, which is referred to in this specification as the cyclophosphite.

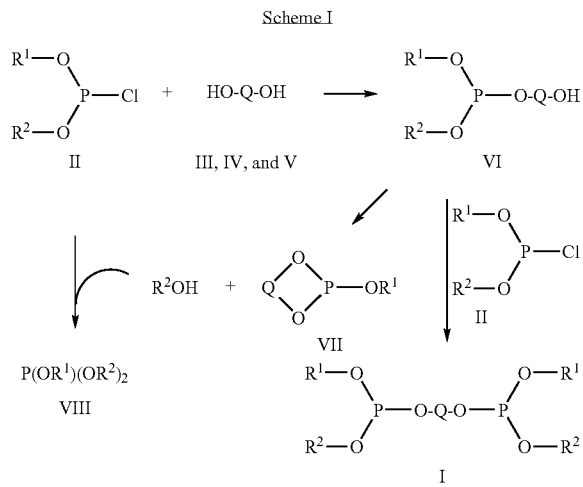

Scheme I

The intramolecular reaction of the monophosphite intermediate produces one equivalent each of the cyclophosphite and aryl alcohol, $R^2OH$, that originates from the phosphorochloridite. At less than complete phosphorochloridite conversions, the aryl alcohol may react with another equivalent of phosphorochloridite to give the acyclic triorganophosphite co-product of Structure VIII, which is referred to in this specification as the triphosphite. This intramolecular reaction of the monophosphite intermediate is thus a yield loss of both the bisaryl compound and the phosphorochloridite needed for diphosphite production and lower selectivities to the diphosphite from the bisaryl compound as a result of the production of triorganophosphites of Structures VII and VIII. Generally, more steric bulk in the bisaryl compound, the phosphorochloridite, or both the bisaryl compound and the phosphorochloridite results in greater amounts of triorganophosphite co-products.

It is to be noted, in the case where $R^1$ and $R^2$ are not the same, $R^1OH$ or $R^2OH$ may be lost from the monophosphite intermediate of Structure VI in the intramolecular reaction, and thus the free aryl alcohol may be $R^1OH$ or $R^2OH$, or a mixture of both. Likewise, the cyclophosphite of Structure VII may contain an $OR^1$ or an $OR^2$ moiety as drawn in Structures VIIa and VIIb. Furthermore, should the phosphorochloridite, $(R^1O)(R^2O)PCl$, not be pure but also include $(R^1O)_2PCl$ and $(R^2O)_2PCl$, the triphosphite co-products of Structure VIII may be selected from the group consisting of $P(OR^1)(OR^2)_2$, $P(OR^1)_2(OR^2)$, $P(OR^1)_3$, $P(OR^2)_3$.

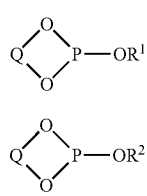

Structure VIIa

Structure VIIb

The invention does not depend upon the method for the synthesis of the phosphorochloridite, which are known in the art. Phosphorochloridites may be synthesized by stepwise reaction of $PCl_3$ with aryl alcohols, $R^1OH$ and $R^2OH$, in the presence of a suitable organic base to first prepare a phosphorodichloridite, for example $(R^1O)PCl_2$, followed by further reaction to prepare the phosphorochloridite, for example $(R^1O)(R^2O)PCl$, which is represented here as Structure II. Selective syntheses for phosphorochloridites of Structure II are disclosed, for example, in PCT Publication WO 2004/050588.

Scheme II shows a generalized reaction scheme for hydrolysis of the phosphorochloridite. Instead of reacting with the bisaryl compound, the phosphorochloridite may react with water in a sequential manner to generate acidic phosphorus-containing compounds (Structures IX and X), phosphorous acid, $H_3PO_3$, and aryl alcohol originating from the phosphorochloridite. The phosphorochloridite may also react with the initial hydrolysis product (Structure IX) to form a phosphorus-containing acid anhydride (Structure XI), also referred to in this specification as POP.

It is to be noted, in the case where $R^1$ and $R^2$ are not the same, $R^1OH$ or $R^2OH$ may be lost during hydrolysis of the acidic compound of structure IX, and thus the free aryl alcohol generated, along with the compound of Structure X, may be $R^1OH$ or $R^2OH$, or a mixture of both. Likewise, the acidic phosphorus-containing compound of Structure X may contain an $OR^1$ or an $OR^2$ moiety and may be a mixture of compounds.

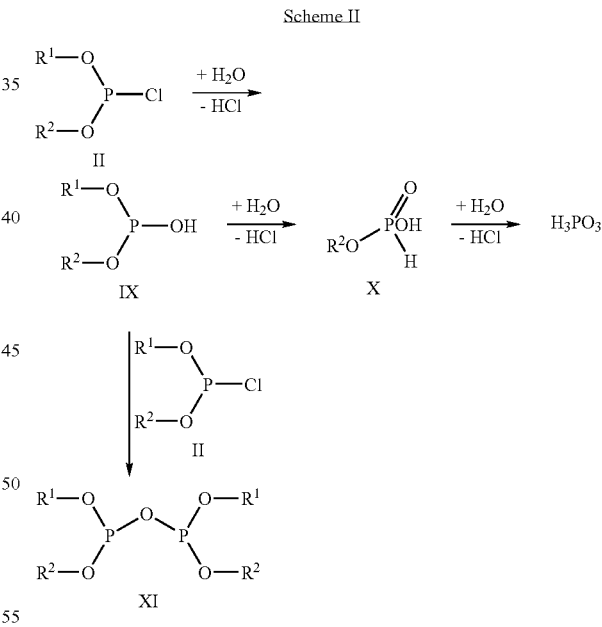

Scheme II

Empirically, as phosphorochloridite conversion increases, the intramolecular reaction rate for conversion of the monophosphite intermediate to cyclophosphite increases and selectivity to the desired diphosphite decreases. At high phosphorochloridite concentration, the rate for conversion of the monophosphite intermediate to diphosphite is increased compared to that in more dilute reaction conditions. Furthermore, dilute solutions offer additional opportunity for water contamination and subsequent formation of acidic phosphorus-containing compounds which may act as catalysts for the undesired intramolecular reaction. Methods for limiting the concentration of the monophosphite intermediate in the reaction mixture is necessary to achieve maximum selectivity to the desired diphosphite. Limiting the concentration of the monophosphite intermediate in the reaction mixture is also a method to limit the formation of co-products such as the cyclophosphite, the triphosphite, and combinations thereof.

While obtaining high selectivities to the diphosphites of Structure I, the present invention provides a method for overcoming the temperature limitations, identified in U.S. Pat. No. 6,069,267 and WO 2004/050588.

The present invention provides a method for producing a diphosphite of Structure I,

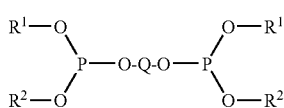

Structure I comprising the steps of:
contacting a phosphorochloridite of Structure II,

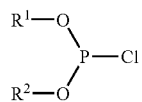

Structure II with a bisaryl compound selected from the group consisting of Structure III, Structure IV, and Structure V,

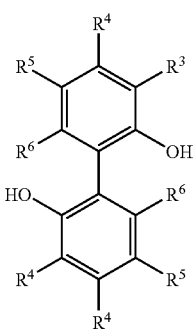

Structure III

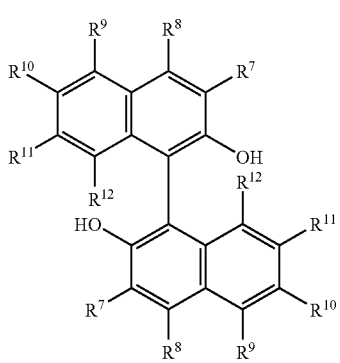

Structure IV

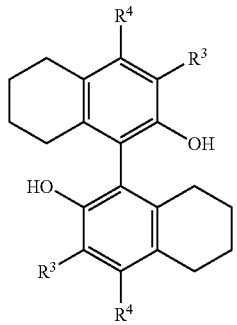

Structure V and a tertiary organic amine, comprising a basic nitrogen atom or a plurality of nitrogen atoms, to produce a reaction mixture comprising a diphosphite of Structure I;
wherein,
the contacting is done by at least one contacting method selected from the group consisting of,
(i). feeding the bisaryl compound to a mixture of phosphorochloridite and tertiary organic amine, and
(ii). feeding the bisaryl compound and the tertiary organic amine either separately or as a mixture to the phosphorochloridite;
and the contacting is done by controlling the feeding such that:
a first mole ratio is at least 2.0 during all stages of the contacting, wherein the first mole ratio is defined as moles of phosphorochloridite in the reaction mixture divided by moles of bisaryl compound fed to the reaction mixture, and
a second mole ratio is at least 1.0 during all stages of the contacting, wherein the second mole ratio is defined as moles of basic nitrogen atoms from the tertiary organic amine fed to the reaction mixture divided by moles of phosphorochloridite in the reaction mixture;
and the method is characterized in that the contacting occurs at a temperature from about 10° C. to about 110° C. to produce the diphosphite in the reaction mixture with a selectivity between 70% and 100% from the bisaryl compound;
wherein,
the selectivity equals moles of diphosphite produced in the reaction mixture divided by total moles of the bisaryl compound contacting the phosphorochloridite;
and wherein in Structures I to V,
$R^1$ and $R^2$ are the same or different, substituted or unsubstituted, monovalent aryl groups; each of $R^3$, $R^4$, $R^5$, $R^6$, $R^7$, $R^8$, $R^9$, $R^{10}$, $R^{11}$, and $R^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogenyl groups; and O-Q-O is a dianion of the bisaryl compound.

Examples of tertiary organic amines comprising a single basic nitrogen atom may be a (R')(R")(R''')N compound wherein R', R", and R''' are independently selected from the group consisting of $C_1$ to $C_{10}$ alkyl and $C_6$ to $C_{10}$ aryl radicals, may be a tertiary aromatic amine compound, for example pyridine, or may be combinations of tertiary organic amines comprising a single basic nitrogen atom. Tertiary organic amines comprising a plurality of basic nitrogen atoms mean that all basic nitrogen atoms of the tertiary organic amine contain no N—H bonds. An example of such a tertiary organic amine is N,N,N',N'-tetramethylethylenediamine.

Contacting methods (i) and (ii) may be performed in semi-batch, continuous flow, or a combination of semi-batch and continuous flow modes. For example, feeding the bisaryl compound continuously or discontinuously to a stirred vessel comprising the phosphorochloridite and tertiary organic amine. For example, feeding the bisaryl compound continuously or discontinuously to a tubular reactor comprising continuous flow of a mixture of the phosphorochloridite and tertiary organic amine.

The phrase "stage of the contacting" for the chemical reaction of this method has its usual meaning wherein an initial stage of the contacting is when all three reactants, phosphorochloridite, bisaryl compound, and tertiary organic amine, first come into contact and a final stage is when the reaction is terminated, for example when water is added to the reaction mixture to separate a tertiary organic amine hydrogen chloride salt from the diphosphite.

The first mole ratio is equal to the moles of phosphorochloridite in the reaction mixture divided by moles of bisaryl compound fed to the reaction mixture. To obtain high selectivities to the diphosphite of Structure I, the contacting is also done by controlling the feeding during all stages of the contacting such that the first mole ratio is at least 2. Below 2 molar equivalents of phosphorochloridite in the reaction mixture, the formation of triorganophosphite co-products can increase which decreases the selectivity to the desired diphosphite. During the stage of the contacting of high phosphorochloridite conversion, for example between 90% and 100%, higher selectivities to the desired diphosphite may also be achieved by controlling the feeding such that the first mole ratio is between 2.1 to 2.7. The phosphorochloridite conversion is defined as 100% multiplied by a total moles of phosphorochloridite in the reaction mixture at the stage of the contacting divided by a total moles of phosphorochloridite undergoing the contacting by the method.

The second mole ratio is equal to the moles of basic nitrogen atoms from the tertiary organic amine fed to the reaction mixture divided by moles of phosphorochloridite in the reaction mixture. To obtain high selectivities to the diphosphite of Structure I, the contacting is also done by controlling the feeding during all stages of the contacting such that the second mole ratio is at least 1. Below 1 molar equivalent, the formation of triorganophosphite co-products can increase which decreases the selectivity to the desired diphosphite. During any stage of the contacting, higher selectivities to the desired diphosphite may also be achieved by controlling the feeding such that the second mole ratio is between 1.0 to 1.5.

In the absence of significant water (>300 ppm by weight) entering the reaction mixture with the bisaryl compound, the tertiary organic amine, aromatic hydrocarbon solvent, hydrocarbon solvent, or a combination of these members, the first and second mole ratios may be controlled within these values by knowing the total moles of phosphorochloridite to be contacted and adjusting the molar feed flows of bisaryl compound, for example, over a specific amount of time. Alternatively, control within these values during the feeding may include withdrawing samples to analyze the liquid reaction mixture by $^{31}P$ NMR and liquid chromatography.

In other aspects of the invention, the contacting of the method occurs at a temperature within a temperature range listed in the left hand column of Table 1. In other aspects of the invention, the contacting of the method occurs at a temperature within a temperature range listed in the right hand column of Table 1. In other aspects of the invention, the reaction mixture further comprises a hydrocarbon solvent and the boiling point of the reaction mixture at one atmosphere (1 atm) in Table 1 is a boiling point of the hydrocarbon solvent. The hydrocarbon solvent may be introduced into the reaction mixture with the phosphorochloridite, bisaryl compound, tertiary organic amine, from any combination of such members, or independent of these reactants.

TABLE 1

Suitable Temperature Ranges for the Contacting Step of the DisclosedMethod.

| Temperature Range | Temperature Range |
|---|---|
| 10 to 110° C. | 10° C. to a boiling point of the reaction mixture (1 atm) |
| 15 to 110° C. | 15° C. to a boiling point of the reaction mixture (1 atm) |
| 20 to 110° C. | 20° C. to a boiling point of the reaction mixture (1 atm) |
| 25 to 110° C. | 25° C. to a boiling point of the reaction mixture (1 atm) |
| 30 to 110° C. | 30° C. to a boiling point of the reaction mixture (1 atm) |
| 35 to 110° C. | 35° C. to a boiling point of the reaction mixture (1 atm) |
| 40 to 110° C. | 40° C. to a boiling point of the reaction mixture (1 atm) |
| 45 to 100° C. | 45° C. to a boiling point of the reaction mixture (1 atm) |
| 50 to 110° C. | 50° C. to a boiling point of the reaction mixture (1 atm) |
| 55 to 110° C. | 55° C. to a boiling point of the reaction mixture (1 atm) |
| 60 to 110° C. | 60° C. to a boiling point of the reaction mixture (1 atm) |

Another aspect of the invention is the method wherein the contacting occurs at one or more temperature ranges of Table 1 to produce the diphosphite in the reaction mixture with a selectivity between 75% and 100% from the bisaryl compound, for example between 80% and 100% from the bisaryl compound, for example between 85% and 100% from the bisaryl compound, for example between 90% and 100% from the bisaryl compound.

Another aspect of the invention is the method wherein the reaction mixture further comprises at least one aromatic hydrocarbon solvent. The aromatic hydrocarbon solvent may be selected from the group consisting of $C_6$ to $C_{18}$ aromatic hydrocarbons. The aromatic hydrocarbon solvent may be selected from the group consisting of aromatic hydrocarbons whose boiling point is between 70° C. and 145° C. at atmospheric pressure.

Another aspect of the invention is the method further comprising controlling the feeding such that a phosphorochloridite concentration is greater than or equal to 0.02 moles per liter in the reaction mixture during the stage of the contacting wherein phosphorochloridite conversion is from 0% to 90%. Again, the phosphorochloridite conversion is defined as 100% multiplied by a total moles of phosphorochloridite in the reaction mixture at the stage of the contacting divided by a total moles of phosphorochloridite undergoing the contacting by the method. Another aspect of the invention is the method of the previous aspect wherein the phosphorochloridite concentration is between 0.02 and 2.0 moles per liter in the reaction mixture during the stage of the contacting wherein phosphorochloridite conversion is from 0% to 90%.

Another aspect of the invention is the method further comprising feeding the bisaryl compound to the phosphorochloridite at a feed rate between 0.04 and 10 molar equivalents per hour, relative to total moles of phosphorochloridite undergoing the contacting by the method. For example, feeding the bisaryl compound to the phosphorochloridite at a feed rate between 0.5 and 10 molar equivalents per hour.

Another aspect of the invention is the method further comprising feeding the bisaryl compound to the phosphorochloridite as a bisaryl solution comprising the bisaryl compound and hydrocarbon solvent. The hydrocarbon solvent may be hydrocarbons selected from the group consisting of linear acyclic $C_5$ to $C_{18}$ aliphatic, branched acyclic $C_5$ to $C_{18}$ aliphatic, unsubstituted cyclic $C_5$ to $C_{18}$ aliphatic, substituted cyclic $C_5$ to $C_{18}$ aliphatic, unsubstituted $C_6$ to $C_{10}$ aromatic, and $C_6$ to $C_{18}$ substituted aromatic hydrocarbons. The hydrocarbon solvent may be selected from the group consisting of hydrocarbons whose boiling point is between 70° C. and 145° C. at atmospheric pressure.

Another aspect of the invention is the method of the previous aspect wherein the reaction mixture further comprises an upper liquid surface, the contacting further comprises providing a stirring shaft comprising at least one impeller attached to the stirring shaft wherein at least one impeller is located below the upper liquid surface, and the feeding further comprises providing rotational energy to the stirring shaft to mechanically stir the reaction mixture. The term "upper liquid surface" may also be viewed as an interface between gas and liquid phases. Apparatus (impellers, stirring shafts) and methods for providing rotational energy to the stirring shaft may be selected from apparatus and methods known in the art.

Another aspect of the invention is the method of the previous aspect further comprising feeding the bisaryl solution to the phosphorochloridite by at least one mixing method selected from the group consisting of, feeding the bisaryl compound to the reaction mixture above the upper liquid surface by flowing the bisaryl solution through at least one liquid distributor that disperses the bisaryl solution over at least a portion of the upper liquid surface;

feeding the bisaryl compound to the reaction mixture above the upper liquid surface by flowing the bisaryl solution through at least one liquid distributor that disperses the bisaryl solution over at least a portion of the upper surface and feeding the tertiary organic amine to the reaction mixture below the upper liquid surface;

feeding the bisaryl compound to the reaction mixture by flowing the bisaryl solution through at least one feed line that directs the bisaryl solution toward an impeller located below the upper liquid surface;

feeding the bisaryl compound to the reaction mixture by flowing the bisaryl solution through at least one feed line that directs the bisaryl solution toward an impeller located below the upper liquid surface and feeding the tertiary organic amine to the reaction mixture by flowing the tertiary organic amine through at least one feed line that directs the tertiary organic amine toward an impeller located below the upper liquid surface; and the bisaryl solution further comprises at least a portion of the tertiary organic amine fed to the reaction mixture and feeding the bisaryl compound to the reaction mixture by flowing the bisaryl solution, further comprising the tertiary organic amine, through at least one feed line that directs the bisaryl solution toward an impeller located below the upper liquid surface.

For the mixing methods, examples of liquid distributors include nozzles, perforated pipes, and downcomer trays. Also, flowing a liquid (bisaryl solution and tertiary organic amine) through at least one feed line that directs the liquid toward an impeller located below the upper liquid surface may help ensure efficient mixing of the liquid with the phosphorochloridite in a turbulent mixing zone of the reaction mixture. Poor mixing of the bisaryl compound or bisaryl solution with the phosphorochloridite may result in localized high concentrations of both bisaryl compound and monophosphite intermediate of Structure VI resulting in poorer selectivities to diphosphite.

Surprisingly, water is detrimental to the selectivity to the desired diphosphite from the bisaryl compound. Another aspect of the invention is the method wherein the bisaryl compound, the tertiary organic amine, or a combination of the bisaryl compound and the tertiary organic amine, contacting the phosphorochloridite further comprise a total of from 0 ppm to 300 ppm by weight of water. If the bisaryl compound, the tertiary organic amine, or a combination of the bisaryl compound and the tertiary organic amine is fed to the phosphorochloridite as a solution comprising an aromatic hydrocarbon or hydrocarbon solvent, then another aspect of the invention is the method wherein the solution further comprises a total of from 0 ppm to 300 ppm by weight of water. Prior to the contacting with the phosphorochloridite, water may be at least partially separated from the bisaryl compound and the tertiary organic amine by phase separation, distillation, azeotropic distillation, contact with dried molecular sieves, and other methods known in the art.

A function of the tertiary organic amine is to neutralize the HCl co-product in the reaction mixture through the formation of a tertiary organic amine hydrogen chloride salt. This function accelerates reaction rates and limits acid-catalyzed chemistries that may reduce selectivities to diphosphite from the bisaryl compound. Another aspect of the invention is the method further comprising precipitating a tertiary organic amine hydrogen chloride salt from the reaction mixture during the contacting. The selection of the tertiary organic amine and contacting in the presence of a hydrocarbon solvent are methods to precipitate a tertiary organic amine hydrogen chloride salt from the reaction mixture.

Another aspect of the invention is the method further comprising producing at least one phosphorus-containing co-product in the reaction mixture selected from the group consisting of $P(OR^1)(OR^2)_2$, $P(OR^1)_2(OR^2)$, $P(OR^1)_3$, $P(OR^2)_3$, a compound of Structure VIIa, and a compound of Structure VIIb,

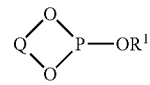

Structure VIIa

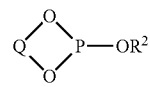

Structure VIIb wherein, less than 30% of the total phosphorus in the reaction mixture is in the form of the at least one phosphorus-containing co-product produced from the contacting. For example, less than 25% of the total phosphorus in the reaction mixture, less than 20% of the total phosphorus in the reaction mixture, less than 15% of the total phosphorus in the reaction mixture, less than 10% of the total phosphorus in the reaction mixture, or less than 5% of the total phosphorus in the reaction mixture is in the form of the at least one phosphorus-containing co-product produced from the contacting.

The invention is illustrated by the following Examples which are not intended to be limiting.

EXAMPLES

The method of diphosphite synthesis of the invention is general. It is most applicable not only to diphosphites having steric hindrance, for example the diphosphites of the Examples, but also applicable to diphosphites with different steric hindrance, diphosphites with less steric hindrance, and unhindered diphosphites.

Diphosphite syntheses were performed in which the relative concentration ratios of amine to bisaryl compound to phosphorochloridite were varied to evaluate the impact on product selectivity. Synthesis and decomposition of the monophosphite intermediate were also investigated. In addition, the concentration of the monophosphite intermediate during diphosphite synthesis was monitored in a series of experiments where the phosphorochloridite concentration was dilute, concentrated, or non-dilute and non-concentrated. These experiments and their results are presented in the following sections.

Most of the experimental results were obtained for the synthesis of the diphosphite shown as Structure Ia in the following reaction scheme. Scheme III is analogous to the generalized Scheme I and includes the phosphorochloridite (Structure IIa), the bisaryl compound (Structure IIIa), the monophosphite intermediate (Structure VIa), the diphosphite (Structure Ia), the cyclophosphite (Structure VIIa), free aryl alcohol, in this case 2,4-xylenol, originating from the phosphorochloridite, and the acyclic triphosphite (Structure VIIIa).

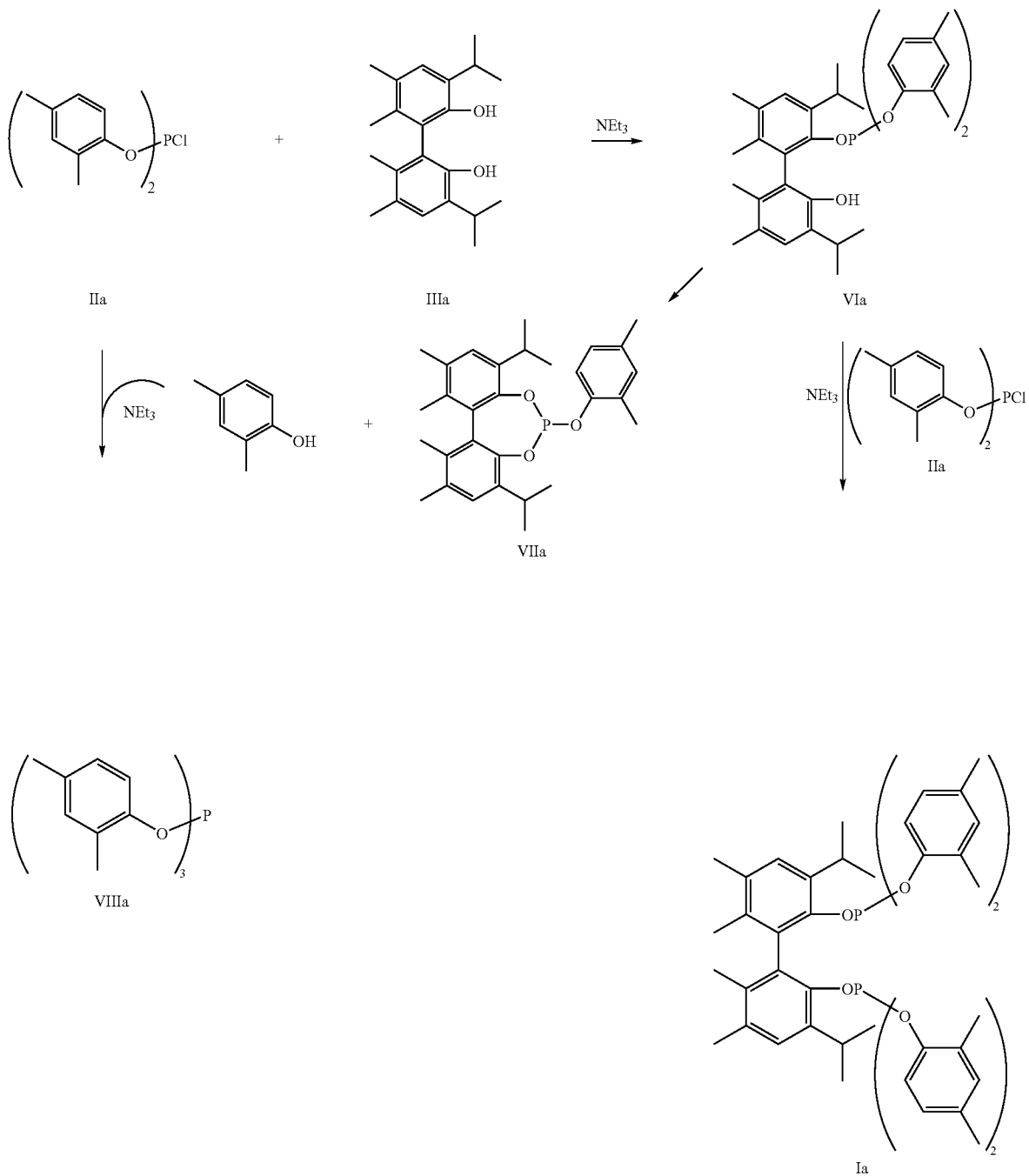

Scheme III

A reaction scheme for the hydrolysis of the phosphorochloridite of Structure IIa is shown below. As an alternative to reacting with a bisaryl compound, the phosphorochloridite can react with successive equivalents of water to generate acidic phosphorus-containing compounds (Structures IXa and Xa), as well as free aryl alcohol, in this case 2,4-xylenol, and $H_3PO_3$. Phosphorochloridite can also react with the first of the hydrolysis products (Structure IXa) to produce a phosphorus-containing acid anhydride (Structure XIa), also referred to as POP.

for minute, "mmol" for millimoles, "mol" for mole, "Monophosphite" for the monophosphite intermediate of Structure VI, VIa, or VIb, "ppm" for part per million by weight, and "rpm" for revolutions per minute. Phosphorodichloridite is abbreviated as $APCl_2$ or $BPCl_2$ where A and B represents an aryloxide moiety derived from an aryl alcohol (e.g., phenol); similarly phosphorochloridite is referred to by Structure numbers II, IIa, or IIb or abbreviated as $A_2PCl$ or ABPCl where A and B represents an aryloxide moiety derived from an aryl alcohol (e.g., phenol). Distributions to various phos-

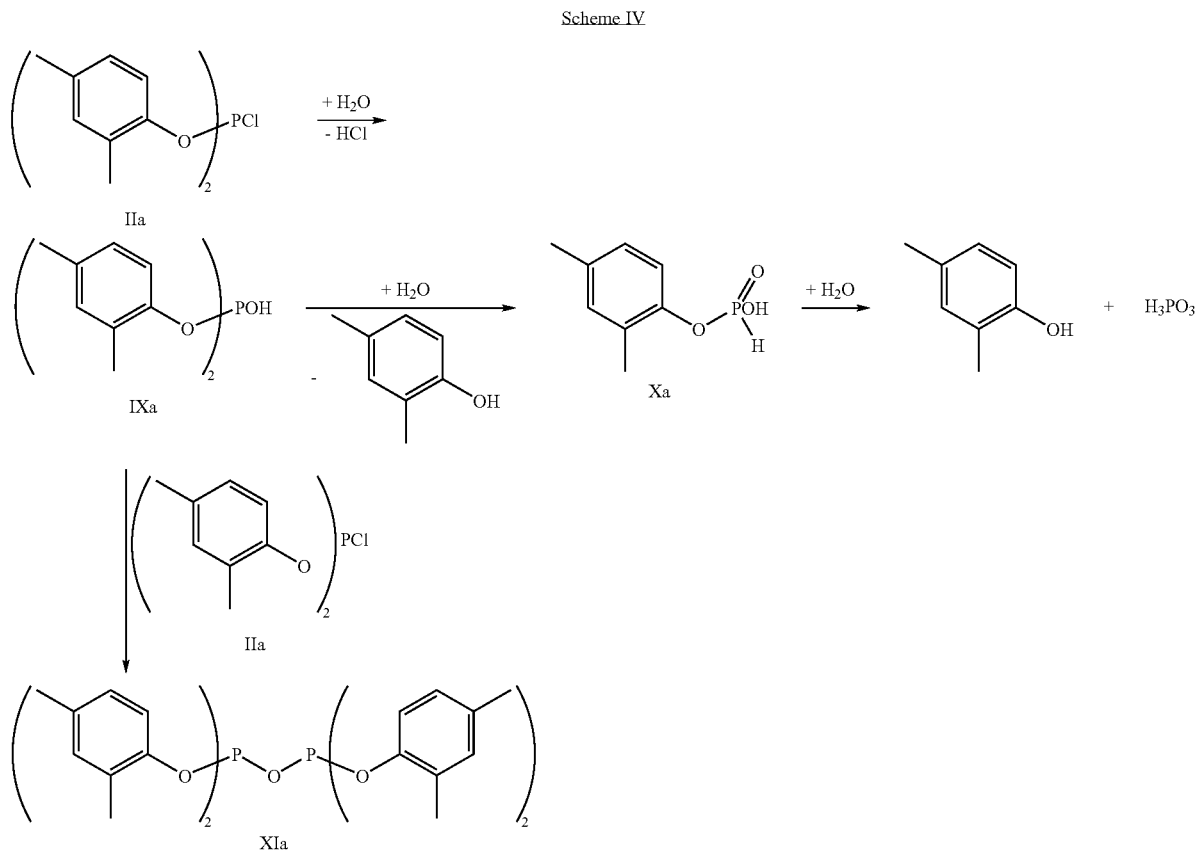

Scheme IV

The numbering of compounds shown in the schemes is used in some of the subsequent Tables. The acidic phosphorus-containing compounds of Structure IXa, of Structure Xa, and $H_3PO_3$ are summed and collectively represented by "H" in the Tables.

It will be recognized that the Structures shown in the reaction schemes are two-dimensional representations of three-dimensional molecules and that rotation about chemical bonds can occur in the molecules to give configurations differing from those shown. For example, rotation about the carbon-carbon bond between the 2- and 2'-positions of the biphenyl bridging group of Structure Ia can bring the two phosphorus atoms in greater or lesser proximity to one another and can allow the phosphite ligand to bind to a single metal atom in a bidentate fashion. The term "bidentate" is well known in the art and means both phosphorus atoms of the ligand are bonded to a single metal atom.

General abbreviations used in the Tables and specification include "~" for about, "conc." for concentration, ° C. for degree Celsius, "equiv." for equivalent(s), "Hr" or "hr" for hour, "Kg" for kilogram, "M" for molar concentration, "min."

phorus-containing species as a percent of total phosphorus in a reaction mixture are measured by quantitative $^{31}P$ NMR analysis of a liquid sample from the reaction mixture. For example, a distribution (% P) for diphosphite=100%×[signal area integral of the $^{31}P$ NMR signal(s) for diphosphite]/[sum of the signal area integrals for the $^{31}P$ NMR signal(s) for all detectible phosphorus-containing compounds], wherein all detectible phosphorus-containing compounds may include $PCl_3$, phosphorodichloridite, phosphorochloridite, diphosphite, monophosphite intermediate, cyclophosphite, triphosphite, POP, and H compounds, if detectible by the $^{31}P$ NMR measurement.

Bisaryl compounds of Structure III, IV, and V, for example the compound of Structure IIIa, may be prepared by any suitable synthetic means known in the art. For example bisaryl compounds of Structure III and IV may be prepared by the oxidative coupling of the corresponding substituted phenol and naphthol, respectively. Bisaryl compounds of Structure V may be prepared by the partial hydrogenation of the corresponding binaphthol compound or oxidative coupling of the corresponding tetrahydronaphthol compound.

Examples 1-6

Order of Addition and Relative Concentration Ratios

The impact of the relative concentration ratios of tertiary organic amine to phosphorochloridite to bisaryl compound on product selectivity is explored through six different addition modes where the order of addition of reactants is varied as the feeds and reactor startup charge. Table 2 indicates which material(s) are added (together, if more than one is listed) as feed to what material(s) in the reactor charge. The syringe pump feed rate, in mL/min, is also given for each Example.

TABLE 2

Modes of Addition and Feed Rates for Examples 1-6.

| Example | Feed Materials | Feed Rate (mL/min) | Added to Reactor Charge of |
|---|---|---|---|
| 1* | IIa, IIIa | 0.30 | Et$_3$N, toluene |
| 1b | IIa, IIIa | 0.30 | Et$_3$N, toluene |
| 2 | Et$_3$N | 0.14 | IIa, IIIa |
| 3 | Et$_3$N, IIIa | 0.17 | IIa |
| 4 | IIa | 0.26 | Et$_3$N, IIIa |
| 5 | IIIa | 0.12 | IIa, Et$_3$N |
| 6 | IIa, Et$_3$N | 0.31 | IIIa, toluene |

*Feed addition at −40° C. For all other experiments, feed addition at +5° C.

All experiments are conducted inside an inert atmosphere glove box using water-free solvents and reactants. All feed solutions are stored over activated molecular sieves to exclude traces of water, for example less than 300 ppm by weight water. Phosphorochloridite is taken from a single source prepared from high purity PCl$_3$ and contained 91.6% phosphorochloridite IIa and 8.4% triphosphite VIIIa by a method of WO 2004/050588. Cyclophosphite VIIa is not present in this single source.

Each experiment uses the following feed and charge amounts and concentrations: 25.00 g of a 0.30 molar (M) phosphorochloridite IIa solution in toluene (solution density 0.87 g/mL), 4.42 g of a 2.0 M triethylamine (NEt$_3$) solution in toluene (solution density 0.824 g/mL), 3.34 g of a 1.0 M bisaryl compound IIIa solution in toluene (solution density 0.907 g/mL), and 8.65 g of toluene. For Examples 1*, 1b, and 6, 8.65 g of toluene are added to the reactor to increase the volume of the initial reactor charge and enable better stirring. For each of these experiments, the total moles of phosphorochloridite charged to the reaction mixture divided by total moles of bisaryl compound charged to the reaction mixture is about 2.3. For each of these experiments, the total moles of basic nitrogen atoms from the triethylamine charged to the reaction mixture divided by total moles of phosphorochloridite charged to the reaction mixture is about 1.25. All experiments are performed at +5° C. except for Experiment 1* which is run at −40° C. After feed addition is complete, the reaction mixtures are allowed to come to room temperature (25° C.) and sampled once more.

Reaction mixture samples, withdrawn during feed addition at different reaction stages and once the reaction mixture reached room temperature at the end of the run, are analyzed via $^{31}$P NMR using triphenylphosphine oxide (TPPO) as an internal standard for quantitative analysis of phosphorus-containing compounds. Any detectable amounts of cyclophosphite VIIa or additional triphosphite VIIIa formed during the experiments are presumed to be derived from the intramolecular reaction of the monophosphite intermediate VIa. For the different addition modes, distributions of major products and intermediates during and after addition are reported in Table 3. The acidic phosphorus-containing compounds of Structure IXa, Structure Xa, and H$_3$PO$_3$ are summed and represented collectively as "H" in all tables. Also reported at different reaction stages is a cumulative selectivity (SEL) for the production of the diphosphite Ia from the bisaryl compound IIIa, defined as moles of diphosphite in the reaction mixture divided by moles of the bisaryl compound fed to the reaction mixture. Through the reaction of the present invention, the dianion of the bisaryl compound, O-Q-O, may be incorporated into three of the phosphorus-containing compounds listed in Table 3, the cyclophosphite, monophosphite intermediate, and diphosphite. So at a specific reaction stage, the selectivity (SEL) for the production of the diphosphite from the bisaryl compound=100%×distribution (% P) for diphosphite/[distribution (% P) for cyclophosphite+distribution (% P) for monophosphite+distribution (% P) for diphosphite]. Alternatively, this selectivity may be determined from a mass balance analysis.

For the reaction of the present invention, less than 30% of the total phosphorus in the reaction mixture is in the form of the at least one phosphorus-containing co-product produced from the contacting, wherein the at least one phosphorus-containing co-product, is selected from the group consisting of P(OR$^1$)(OR$^2$)$_2$, P(OR$^1$)$_2$(OR$^2$), P(OR$^1$)$_3$, P(OR$^2$)$_3$, a compound of Structure VIa, and a compound of Structure VIb. The total phosphorus in the reaction mixture

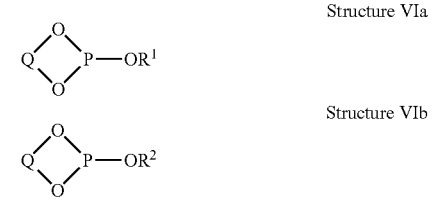

Structure VIa

Structure VIb in the form of the at least one phosphorus-containing co-product may also be calculated from such measured distribution (% P) data with an adjustment for the amount of triphosphite, if present, entering the reaction of the present invention with the phosphorochloridite, designated "triphosphite impurity". The "triphosphite impurity" is not produced from the contacting of the present invention, but rather the contacting of PCl$_3$ and/or (RO)PCl$_2$ with an aryl alcohol as discussed earlier. So at a specific reaction stage, the % of phosphorus in the form of the at least one phosphorus-containing co-product=100%×(sum of the distribution (% P) for each phosphorus-containing co-product−distribution (% P) for triphosphite impurity)/[sum of the distribution (% P) for each phosphorus-containing co-product−distribution (% P) for triphosphite impurity+distribution (% P) for diphosphite]. For example for the data in the last row of Table 6, the % of phosphorus in the form of the at least one phosphorus-containing co-product=100%×(3.2%+7.8%−5%)/[3.2%+7.8%−5%+85.8%]=6.5%. Alternatively, the % of phosphorus in the form of the at least one phosphorus-containing co-product may be determined by analyzing a liquid sample from the reaction mixture by reverse-phase high-pressure liquid chromatography.

In Example 5, only 1% of the total phosphorus is in the form of the cyclophosphite during the course of the addition and the amount of triphosphite increased by the same value. The highest level of the cyclophosphite and triphosphite formation is found in addition modes where buildup of monophosphite VIa was substantial. In Example 4, where phosphorochloridite is added to a mixture of bisaryl compound IIIa and triethylamine, the distribution to the monophosphite intermediate VIa was up to 75%, and about 4% cyclophosphite and additional triphosphite are formed via the intramolecular reaction of the monophosphite intermediate VIa. Generally, this intramolecular reaction is surprisingly low and could be attributed to low moisture levels and excess triethylamine, both of which may reduce the intramolecular reaction rate if it is catalyzed by one or more acidic phosphorus-containing compounds. Especially under conditions where bisaryl compound is added to triethylamine and phosphorochloridite in the absence of water or acidic phosphorus-containing compounds, the intramolecular reaction of the monophosphite intermediate VIa does not appear kinetically competitive, relative to production of the diphosphite Ia. A peculiar effect of seemingly substoichiometric amounts of bisaryl compound leading to quantitative conversion of phosphorochloridite is usually limited to smaller scales, especially under dilute conditions, and vanishes starting at the 2000 mL scale.

Examples 7-13

Synthesis of the Monophosphite Intermediate and the Intramolecular Reaction

Monophosphite intermediate VIa is synthesized independently and its reactivity investigated by $^{31}$P NMR spectroscopy. Under reaction conditions in which the bisaryl compound is added to phosphorochloridite and triethylamine, the monophosphite intermediate VIa was not observed by $^{31}$P NMR spectroscopy. However, the monophosphite intermediate VIa is observed in the reaction mixture at low phosphorochloridite concentrations, which corresponds to any reaction condition providing high conversion of the phosphorochloridite in the reaction mixture.

Therefore, monophosphite intermediate VIa is synthesized by adding a toluene solution of 1 molar equivalent phosphorochloridite IIa and 1.25 molar equivalents triethylamine to a toluene solution containing 1 molar equivalent of the bisaryl compound IIIa at −35° C. in a dry-atmosphere environment. The monophosphite intermediate solution contains 65% monophosphite, 1-2% cyclophosphite, 17% diphosphite, and 15% triphosphite (relative concentrations 97% monophosphite and 3% cyclophosphite). The compounds within this monophosphite intermediate solution are stable at a temperature of −35° C. without a change in the composition even when samples are warmed to room temperature for $^{31}$P NMR analysis. A parallel sample kept at room temperature for an extended period of time show no detectable change in the concentrations of monophosphite intermediate and cyclophosphite within 1 hour but quantitative conversion is observed over a time period of 68 hours. A freshly prepared monophosphite intermediate solution is stored at −35° C. and used for each experimental study of its reactivity.

In an initial experiment, the monophosphite intermediate VIa of a monophosphite intermediate solution is treated with a mixture of 1 molar equivalent each of phosphorochloridite and triethylamine at −10° C. to +20° C. Subsequent NMR analysis of the reaction solution shows quantitative conversion of the monophosphite intermediate to the diphosphite, independently reconfirming the species, characterized as having a $^{31}$P NMR shift about 0.25 ppm lower than that for the cyclophosphite VIIa, as the monophosphite intermediate on the pathway to diphosphite.

In a separate experiment, a monophosphite intermediate solution containing 0.024 mmol monophosphite intermediate in toluene is treated with 0.28 mmol H$_2$O then mixed at room temperature. After 20 minutes, less than 10% of the monophosphite intermediate had been converted to cyclophosphite (Table 4, Example 11). This experiment is repeated in the presence of 0.16 mmol triethylamine with the same result, indicating that the intramolecular reaction of monophosphite intermediate is not catalyzed by base (Table 4, Example 12). However, when a solution of 0.024 mmol phosphorochloridite and 0.16 mmol triethylamine is added to a mixture of 0.024 mmol monophosphite intermediate and 0.28 mmol H$_2$O in toluene (Table 4, Examples 7-10), 40% decomposition was observed within 16 minutes. The intramolecular reaction slowed after an initial period and displayed a zero order kinetic behavior. When the same experiment was repeated in the absence of triethylamine, the intramolecular reaction of monophosphite intermediate was instantaneous (Table 4, Example 13).

While not wanting to be bound by theory, these experiments lead to the conclusion that during diphosphite synthesis, the intramolecular reaction of monophosphite intermediate is catalyzed by acid and, most likely by hydrolysis products derived from the reaction of water and phosphorochloridite. The decomposition reaction is fast in the absence of triethylamine but retarded in the presence of triethylamine. Using superstoichiometric amounts of triethylamine during diphosphite synthesis starting from the bisaryl compound and the phosphorochloridite can limit monophosphite intermediate conversion to cyclophosphite. When phosphorochloridite concentrations drop below a threshold limit, the catalytic intramolecular reaction of the monophosphite intermediate, although retarded by triethylamine, can become kinetically competitive relative to diphosphite production and lead to significant cyclophosphite build-up.

Example 14

Diphosphite Synthesis Under Dilute Conditions

To determine the onset of monophosphite intermediate build-up during diphosphite synthesis, a dilute synthesis experiment is conducted under strictly water-free conditions in a glove box with syringe pumps and the transformation of built-up monophosphite intermediate was followed over time by $^{31}$P NMR analysis. A solution of 9.6 mL of a 0.5 M PCl$_3$ (1 molar equivalent) in toluene and 10 mL toluene is treated with 32 alternate portions each of 0.6 mL of a 0.5 M triethylamine solution in toluene and 0.6 mL of a 0.5 M 2,4-xylenol solution in toluene at an addition rate of 0.1 mL/minute, following the phosphorochloridite synthesis method disclosed in published application WO 2004/050588. The reaction mixture is stirred in a baffled, 125 mL reactor and kept at −30° C. The resulting phosphorochloridite solution showed 95% phosphorochloridite and 5% triphosphite by $^{31}$P NMR. This solution is then treated with 1.16 molar equivalents of triethylamine (10.6 mL, 0.5 M solution in toluene) and kept at +10° C. At this point, the phosphorochloridite concentration is about 0.067 mol/L. With stirring, a 0.5 M bisaryl compound solution in toluene is added at 0.1 mL/min in 0.45 mL portions for a total amount of 4.24 mL (0.46 molar equivalents). NMR samples are taken at several stages of the bisaryl compound addition. When the monophosphite intermediate are observed by $^{31}$P NMR, the addition of bisaryl compound is interrupted until the conversion of monophosphite intermediate is complete.

Table 5 gives representative $^{31}$P NMR resonances of the reported phosphorus species, the distribution of which, as derived from $^{31}$P NMR measurements, is give in Table 5. The $^{31}$P NMR resonances of the reported phosphorus species are applicable to the results for other Examples as well. Table 6 shows the corresponding differential conversion, which indicates satisfactory mass balance accounting.

The build-up of significant amounts of monophosphite (>1% phosphorus) at a lower limit phosphorochloridite concentration of about 0.03 to about 0.02 mol/L in the reaction mixture, as seen in this dilute experiment, is consistent with standard runs under conditions where feeds and initial reactor charge are four times as concentrated. Independent of scale and concentration, provided sufficient triethylamine is used, the monophosphite intermediate is accumulating (>1% total phosphorus) once phosphorochloridite concentrations fall below about 0.03 mol/L, for example below about 0.02 mol/L, in the reaction mixture. In this particular dilute experiment, the critical cyclophosphite concentration accompanied by monophosphite intermediate build-up was reached at about 58% phosphorochloridite conversion, reflecting the addition of 56% of the total bisaryl compound feed. Reducing the bisaryl compound feed rate will affect the amount of monophosphite intermediate build-up since the diphosphite production will catch up with monophosphite intermediate production. If the concentration of the monophosphite intermediate has built-up, decreasing the bisaryl compound feed rate is a means for limiting the concentration of the monophosphite intermediate in the reaction mixture. The decrease in addition rate may be gradual or sudden, and may be made in a continuous or a non-continuous manner. Once the excess monophosphite has reacted away, the addition rate of the bisaryl compound can be adjusted, that is, increased or decreased, to a rate sufficient to limit the concentration of the monophosphite intermediate in the reaction mixture.

TABLE 5

Phosphorus Species and Their Representative $^{31}$P NMR Resonances (ppm) Relative to Triphenylphosphine Oxide Internal Standard.

| Phosphorus Species | $^{31}$P Resonance (ppm) |
|---|---|
| PCl$_3$ | 202 |
| APCl$_2$* | 182 |
| A$_2$PCl (IIa)* | 164 |
| Cyclophosphite (VIIa) | 136.8 |
| Monophosphite (VIa) | 136.4 |
| Diphosphite (Ia) | 133 |
| Triphosphite (VIIIa) | 132 |
| POP | 128 |
| H | 0.5 |

*A is 2,4-dimethylphenoxide in these compounds.

Example 15

Diphosphite Synthesis Under Non-Dilute, Non-Concentrated Conditions

Phosphorochloridite IIa is synthesized following a method disclosed in WO 2004/050588 using a concurrent addition method in its simultaneous addition version instead of the 32-step alternating portion version of Example 14 to produce a 0.27 M phosphorochloridite solution comprising about 380 mmol of phosphorochloridite and about 20 mmol of the triphosphite. This experiment is carried out in a 2 L reactor under dry N$_2$ but not inside a dry atmosphere glove box.

About 1.06 molar equivalents of triethylamine, with respect to the detected amount of phosphorochloridite, are added prior to the addition of 1 M solution of bisaryl compound IIIa in toluene. The feeding of the bisaryl compound solution is executed using a peristaltic pump. The total amount of bisaryl compound to be fed is predetermined and calculated to allow for 100% conversion of phosphorochloridite at the final stage of the reaction. Reaction samples are taken periodically during the feeding of the bisaryl compound solution. For the reaction samples, the amount of bisaryl compound added is determined by the differential weight of the feed bottle (which had a potential error associated with it). The distribution of phosphorus species was derived from $^{31}$P NMR measurements (Table 8).

The high levels of POP and acidic phosphorus-containing compounds H seen in two of the reaction samples are believed to result from error in the sampling technique and are not believed to reflect water contamination of the reactor contents. For this reason, for calculations of phosphorochloridite concentration, POP and H levels are accounted for as phosphorochloridite. If NMR resolution is not sufficient to achieve baseline separation between triphosphite and diphosphite signals in these measurements, a correction is made based upon the amount of triphosphite from the previous phosphorochloridite synthesis step and the valid assumption that an increase for triphosphite in the phosphorus distribution during diphosphite synthesis os a direct result of monophosphite intermediate conversion to cyclophosphite. In other words, an additional equivalent of cyclophosphite is formed for every additional equivalent triphosphite observed.

Similar to the experiment performed at a starting concentration of 0.067 mol/L (Example 14), in Example 15 the monophosphite intermediate VIa is observed at a phosphorochloridite concentration of about 0.03 mol/L and below in the reaction mixture. As in most cases, monophosphite intermediate accumulation (10 mmol) is accompanied by a corresponding increase in the cyclophosphite (9 mmol). As the data displayed in Tables 9 and 10 indicate, the amount of cyclophosphite formed at 88% phosphorochloridite conversion equals the additional amount of triphosphite formed during the bisaryl addition. At 88% phosphorochloridite conversion, about 53 mmol of phosphorochloridite is left and the remainder of the bisaryl compound (49 mmol) is added (compare Table 9) resulting in an increase of 51 mmol diphosphite (96% selectivity from the bisaryl compound). After all the phosphorochloridite is consumed, the remaining 12 mmol of monophosphite intermediate was converted to cyclophosphite. It appears that such an intramolecular reaction of the monophosphite intermediate at 88% is triggered by small amounts of hydrolysis products and most of the catalyst is consumed at about 50% of the monophosphite decomposition. For the remainder for the addition period of the bisaryl compound, the amount of monophosphite intermediate stays approximately constant at a level of 11 mmol before slow conversion occurs after reaction completion.

In this case at the 2000 mL scale, the theoretically expected amount of bisaryl compound (190 mmol) reacts with the detected amount of phosphorochloridite (380 mmol) and no negative discrepancy between the calculated and actually needed amount of bisaryl compound to convert all of the phosphorochloridite is observed.

Example 16

Diphosphite Synthesis Under Concentrated Phosphorochloridite Conditions

In this experiment, similar to Example 15 but at a higher starting concentration for the phosphorochloridite solution (0.35 mol/L), the bisaryl compound is added as a more dilute solution (0.5 M versus 1 M previously). The more dilute bisaryl solution is employed to avoid possible mixing problems with the thick suspension of triethylamine hydrochloride solids generated during the bisaryl addition. The same equipment is used as in Example 15. About 1.15 equivalents of triethylamine, with respect to the detected amount of phosphorochloridite (93%) and phosphorodichloridite (2%), are added prior to the bisaryl addition. The phosphorochloridite distribution before the addition of the bisaryl solution amounted to 95% of all phosphorus species. The amount of bisaryl compound added is determined by the differential weight of the feed bottle and the distribution of phosphorus species is derived from $^{31}$P NMR measurements (Table 11).

When compared to the previous run, less conversion of monophosphite intermediate to cyclophosphite is expected using a more concentrated phosphorochloridite solution. However, 3% cyclophosphite formation is observed after reaction completion. This could be explained by the relatively high levels of hydrolysis products, POP and H, observed during the addition of the bisaryl compound. Hydrolysis products POP and H are accounted for in part as phosphorochloridite. It is assumed that 12 mmol of hydrolysis products are present in the reaction mixture and the phosphorochloridite. This is reflected in the corrected phosphorochloridite mass balance and conversion columns of Tables 12 and 13. In this case, hydrolysis products are assumed to be present in the reactor and were only partially a result of sampling procedures.

The amount of hydrolysis product can be estimated by the transformation of bisaryl to diphosphite or monophosphite at high phosphorochloridite conversion, or the absence thereof. After adding 0.38 molar equivalents of bisaryl compound, relative to the total moles of phosphorochloridite undergoing the reaction, the $^{31}$P NMR analysis shows a phosphorus distribution of 83% diphosphite, 2% cyclophosphite, 10% triphosphite, and a 4% total of hydrolysis products POP and H. If the entire amount of 4% hydrolysis products are present in the reactor, an additional charge of bisaryl compound equaling the amount of hydrolysis product should not change the distribution. However, if the hydrolysis products are at least partially generated from phosphorochloridite during the sampling procedure, additional bisaryl compound should react with phosphorochloridite and change the phosphorus distribution. In this experiment, adding an additional portion of 10 mmol (0.013 equivalents) of bisaryl compound to give a cumulative addition of 0.41 equivalents does not change the phosphorus distribution. About 3% of hydrolysis products remain and it is assumed that about 3% of the phosphorus present during the addition of bisaryl compound can be attributed to phosphorochloridite hydrolysis to produce POP and H.

The source of moisture causing hydrolysis during this run is unknown, but based upon $^{31}$P NMR data, it is believed to be most likely a result of water-contaminated triethylamine added immediately before the bisaryl feed is started or a result of a moisture contaminated feed line for the bisaryl solution. Consistent with previous results, the onset of significant conversion of monophosphite intermediate to cyclophosphite is observed at a phosphorochloridite concentration of about 0.02 mol/L where instantly a phosphorus distribution of 4% cyclophosphite was detected.

Relative concentrations of phosphorochloridite to bisaryl compound are important for the formation and accumulation of monophosphite. If monophosphite accumulation is accompanied by adventitious hydrolysis, decomposition to cyclophosphite can occur under acidic conditions. Mixing and feed rates would be expected to influence local concentrations especially in highly viscous reaction suspensions as at the end of the bisaryl compound addition and could potentially impact selectivity. These factors are investigated using a 500 mL baffled reactor with overhead stirring and cooling mantle in a setup similar to that described for the 2000 mL scale experiments in the previous section.

Examples 17-25

Amine Concentration, Mixing Rate, and Bisaryl Addition Rates

Parameters for evaluation in a first set of experiments are amine concentration, mixing rate as determined by the rotation speed of the impeller on the stirring shaft, and feed rate of the bisaryl compound at two different temperatures. Triethylamine, PCl$_3$, and toluene solvent are used as received (anhydrous) from Aldrich.

For all the runs, a correction of the feed is made, where necessary, to remove any phosphorodichloridite APCl$_2$, where A is 2,4-dimethylphenoxide, as the phosphorodichloridite reacts with the bisaryl compound to produce cyclophosphite. Phosphorochloridite distributions are at least 90 mol % of the total phosphorus as derived from $^{31}$P NMR measurements. In an initial attempt to provide conditions perceived to cause substantial monophosphite intermediate accumulation and potential conversion to cyclophosphite, the critical reaction parameters are set to low temperature, insufficient agitation, fast feed rates for the bisaryl compound, and a substoichiometric triethylamine charge.

To determine the necessary amount of excess tertiary organic amine, the range of 0.87 to 1.37 equivalents of triethylamine is investigated where one equivalent was defined as the amount of available chloride in phosphorochloridite A$_2$PCl and phosphorodichloridite APCl$_2$, if present. The triethylamine is added to the phosphorochloridite directly before the addition of the bisaryl compound.

Two different mixing conditions, defined by the rotation speed of the impeller, are studied: 470 rotations per minute (rpm), resulting in ample mixing as indicated visually by a good vortex), and 240 rpm, conditions where a vortex is not observed. Two initial temperatures for bisaryl compound addition were investigated: +20° C. and −20° C. It is appears that especially at high conversions of the bisaryl compound, the monophosphite intermediate is consumed slowly below −10° C. The addition rate for the bisaryl compound is also varied. The bisaryl compound is added to the phosphorochloridite at two different feed rates of 5 molar equivalents per hour and a second faster feed rate of 15 molar equivalents per hour, both relative to the total moles of phosphorochloridite charged to the reaction flask. It appears that reducing the feed rate for the bisaryl compound at the onset of monophosphite intermediate and cyclophosphite formation seems to reduce the rate of cyclophosphite formation and allow for monophosphite intermediate consumption to produce diphosphite in higher selectivity. Diphosphite synthesis conditions and resulting cyclophosphite distribution are presented in Table 14, where cyclophosphite % P distribution reflects the percent phosphorus measured as the cyclophosphite as a fraction of the total phosphorus detected by a $^{31}$P NMR measurement.

For Example 17, where the bisaryl compound is added at a rate of 15 equivalents per hour at −20° C. using a substoichiometric triethylamine charge (0.89 equivalents) and inadequate mixing, the amount of cyclophosphite formed during the reaction was 12.9 mol % by $^{31}$P NMR. Example 22 is conducted at +20° C. using 1.34 equivalents of triethylamine, adequate mixing, and a bisaryl addition rate of 5 equivalents/ hr. In this case, only 2.1 mol % cyclophosphite is formed. The results in Table 14 show that, when at least one equivalent of triethylamine is added, the detected cyclophosphite concentration is not greater than about 7.8 mol % by $^{31}$P NMR. The slower addition rate (5 equivalents/hour) at +20° C. is preferred over the faster addition rate (15 equivalent/hour). Using about 1.1 molar equivalents of triethylamine per mole of phosphorochloridite charged to the reaction flask prevents a measurable conversion of monophosphite intermediate to cyclophosphite during the bisaryl addition phase. Both experiments with substoichiometric amounts of triethylamine, Examples 17 and 24, produce significantly higher levels of cyclophosphite, 12.9% and 19.7%, respectively. Water contamination during this series of experiments is not considered and although there was no indication of significantly different levels of hydrolysis products between experiments (~2% of total phosphorus in NMR samples) different levels of water contamination might have also contributed to the variability in yields. Example 25 represents an atypical result for diphosphite synthesis since a super-stoichiometric amount of bisaryl is added at a high rate.

Examples 26-29

Excess Amine, Mixing Rate, and Bisaryl Addition Rates for a Sterically Bulkier Analogue In Examples 26-29, the fraction of the total detected phosphorus species present as the cyclophosphite, as determined by $^{31}$P NMR, under different addition conditions for the bisaryl compound is examined for a more sterically bulky analogue of diphosphite Ia. In this analogue of Structure Ib as shown in Scheme VI, one of the 2,4-dimethylphenoxide groups on each phosphorus atom of Structure Ia is replaced with one 2-iso-propyl-5-methylphenoxide group derived from thymol. The diphosphite of Structure Ib is obtained by reacting bisaryl compound IIIa with the mixed phosphorochloridite IIb of Scheme V (ABPCl) which in turn is derived from the reaction of PCl$_3$ with thymol and 2,4-xylenol. Relative to 2,4-xylenol, the more sterically bulky thymol group might facilitate the elimination of a free aryl alcohol from the corresponding monophosphite intermediate and increase cyclophosphite (Structures VIIa and VIIb) formation while, at the same time, causing a reduced reaction rate to the monophosphite intermediate relative to that of the analogous diphosphite compound Ia. Other aryloxide groups of comparable steric bulk would be expected to provide comparable results.

For the synthesis of diphosphite Ib, the same methodology as for the synthesis of diphosphite Ia is used. Following a method disclosed in published patent application WO 2004/050588, the intermediate phosphorodichloridite BPCl$_2$ of Scheme V is generated by feeding one molar equivalent each of thymol (as a 2 M solution in toluene) and triethylamine (as a 2 M solution in toluene) separately and concurrently to one molar equivalent of a PCl$_3$ solution in toluene. The 2 M triethylamine solution is fed below the surface of the reaction mixture. The resulting phosphorodichloridite solution (>98%, BPCl$_2$) is treated in the same fashion with one molar equivalent each of 2,4-xylenol (as a 2M solution in toluene) and triethylamine (as a 2M solution in toluene) to generate the mixed phosphorochloridite of Structure IIb (ABPCl of Scheme V).

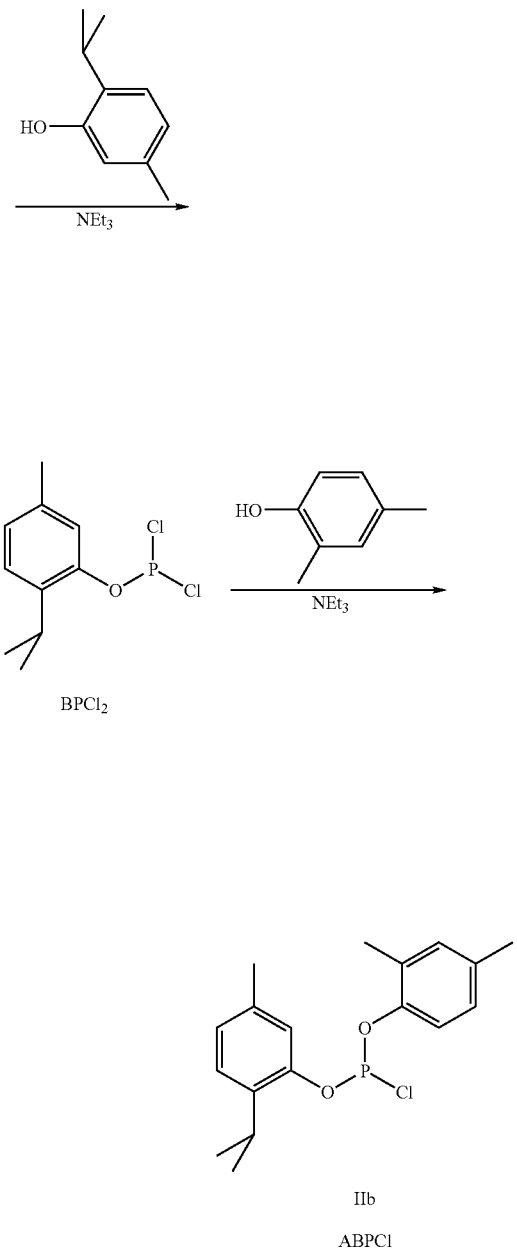

Scheme V

According to $^{31}$P NMR, the resulting phosphorochloridite IIb solution comprises 92-94% of the phosphorochloridite IIb (ABPCl) and about 1% of the phosphorodichloridite (BPCl$_2$). This phosphorochloridite IIb solution is then treated with triethylamine and the bisaryl compound IIIa according to the reaction conditions indicated in Table 15. The phosphorus distributions (% P) for each Example are also given in Table 15. Reaction pathways to the monophosphite intermediate (Structure VIb), the diphosphite (Ib), and possible cyclophosphites (Structures VIIa and VIIb) are shown Scheme VI. The relative amounts of the possible cyclophosphites are determined by the reaction conditions under which they are formed and the steric bulk of the 2,4-dimethylphenoxide versus 2-iso-propyl-5-methylphenoxide groups.

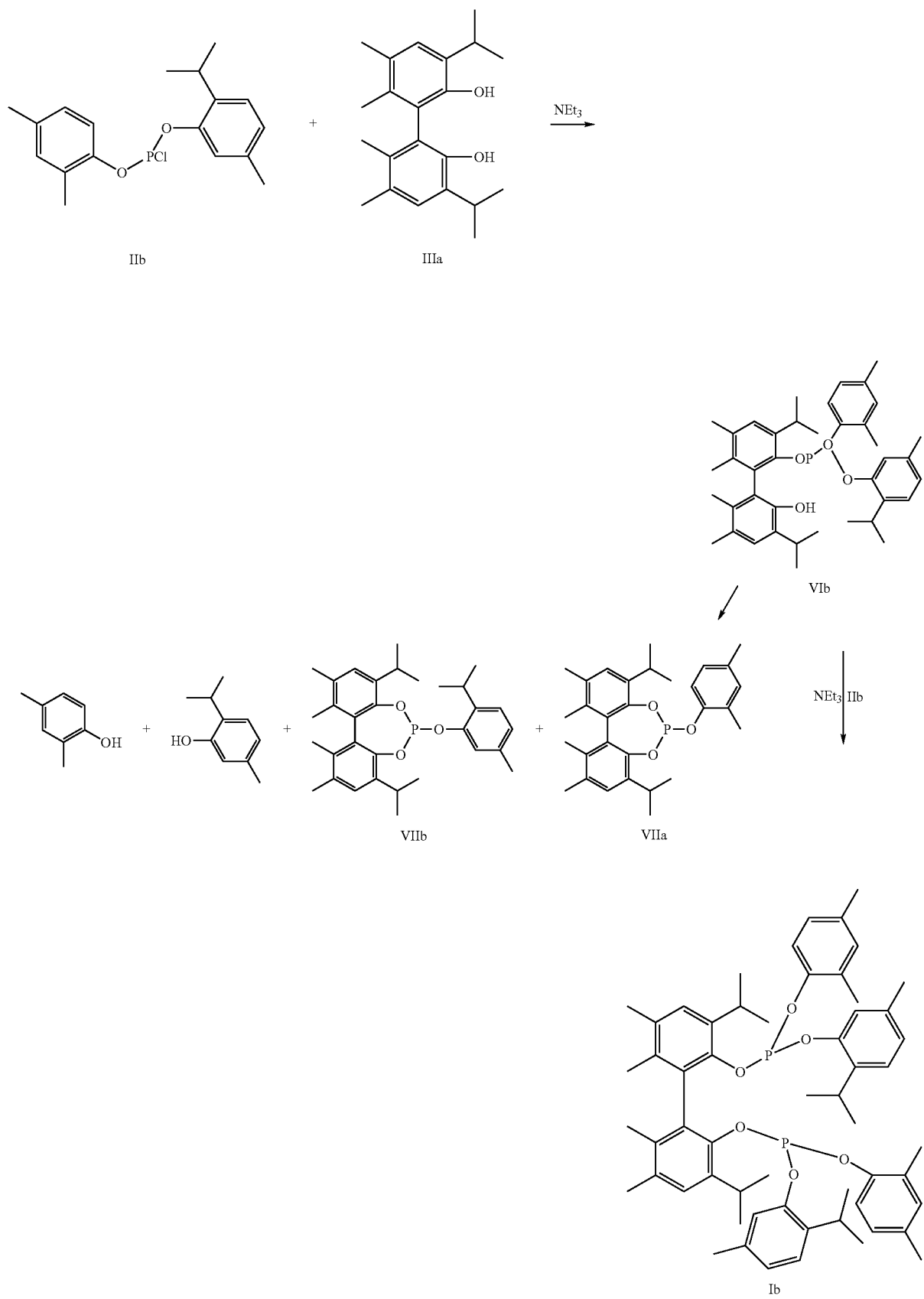

The robustness of the diphosphite synthesis method for this more sterically hindered diphosphite Ib, relative to diphosphite Ia, is tested under the premise that ample triethylamine limits the conversion of the monophosphite intermediate to cyclophosphite under most circumstances. In Examples 26-29, the entire triethylamine charge is added to the phosphorochloridite IIb in the reaction flask (triethylamine to phosphorochloridite IIb mole ratio was 1.3 to 1.4 equivalents) before the addition of the bisaryl compound IIIa commenced. $^{31}$P NMR results indicated that the use of at least 1.3 molar equivalents of triethylamine, relative to the phosphorochloridite IIb charged to the reactor, successfully limits conversion of the sterically hindered monophosphite intermediate to the cyclophosphites of Structures VIIa and VIIb.

Examples 30-39

Reactant Concentration and Water Contamination

Triethylamine levels in conjunction with water contamination play an important role for the selectivity to diphosphite. Water contamination during diphosphite synthesis can result in the formation of acidic phosphorus-containing compounds derived from the phosphorochloride. Whereas excess triethylamine and phosphorochloride promotes the formation of phosphorus-containing acid anhydride, POP, the acidic phosphorus-containing compounds are formed preferentially under acidic conditions. In most cases of adventitious water contamination, both POP and acidic phosphorus-containing compounds are present.

The absolute concentration of the reagents and substrates also impacts the selectivity to the diphosphite. As discussed in a previous section, while not to limit the scope of the invitation by a recitation of theory, selectivity is believed to be directly related to the inter- and intramolecular reactions of the monophosphite intermediate. The rate of acid-catalyzed conversion of the monophosphite intermediate to cyclophosphite versus base-catalyzed and base-driven conversion of the monophosphite intermediate to diphosphite is believed to determine selectivity in diphosphite synthesis. If acid catalysis is fast compared to all other reaction steps, higher dilution should favor monophosphite intermediate conversion to cyclophosphite and dilute experiments, unless done in the absence of traces of water, should result in lower selectivity to diphosphite.

Furthermore, unreacted bisaryl compound in the reaction mixture may also play a role in the catalytic decomposition of monophosphite, for example as a carrier for adventitious water, facilitating the hydrolysis of phosphorochloridite in toluene solution and the monophosphite decomposition by hydrogen bonding between water and the acidic phosphorus-containing compounds. Therefore, feed rates for the bisaryl compound should be considered when exploring the impact of phosphorochloridite concentration and water contamination on selectivity to diphosphite.

A series of experiments to investigate the impact of concentration (varied by the concentration of feed solutions and reactor charge) and water contamination is conducted, wherein the triethylamine amount was kept approximately constant at 1.4 molar equivalents of triethylamine per molar equivalent of phosphorochloridite.

The $^{31}$P NMR results for each process step of Example 30 are given in Table 16. In Example 30, to investigate the impact of water contamination, a reaction solution of phosphorochloridite IIa is deliberately exposed to water before the addition step of bisaryl compound IIIa. Phosphorochloridite is synthesized in a stepwise fashion as previously described and as disclosed in published application WO 2004/050588 using 2.0 M 2,4-xylenol and 2.0 M triethylamine separate feeds to a 1 M PCl$_3$ solution as an initial charge to the reactor, which provides a 0.27 M phosphorochloridite solution. Subsequently, 30 mmol of water are added to the reaction mixture followed by 1.4 molar equivalents of triethylamine, relative to phosphorochloridite. The water addition results in the formation of 15.6% acidic phosphorus-containing compound or compounds (presumably Structure IXa of Scheme IV from hydrolysis of the phosphorochloridite). In other words, 31 mmol of at least one acidic phosphorus-containing compound (assumed to be that of Structure IXa) is detected by $^{31}$P NMR in good agreement with the amount of water added. This method is used for the other experiments to estimate the amount of purposefully induced hydrolysis and was noted as "Equiv. water" in Tables 16-21. Upon addition of 1.4 equivalents of triethylamine, most of the compound of Structure IXa reacts with more phosphorochloridite to form POP (Structure XIa) with about 3% phosphorus remaining as acidic phosphorus-containing compounds. Under the overall basic conditions resulting from using a considerable excess of triethylamine, the cyclophosphite formation during the addition of the bisaryl compound remained negligible at about 1-2% and the total selectivity of diphosphite from the bisaryl compound is about 97%. However, compared to previous runs at the same concentration, the addition of the bisaryl compound to the reaction mixture in this Example was conducted in portions. About 65 g of a 1 M bisaryl compound solution in toluene (72 mmol=0.75 equiv. for 1 equiv of A$_2$PCl) was added in stages (see Table 15) to avoid build up of unreacted bisaryl compound. Addition rates are 0.23 molar equivalents/hour followed by 0.06 equivalents/hour and 0.03 equivalents/hour with time intervals between the addition periods of at least 2 hours to assure complete reaction of each added portion of the bisaryl compound. Despite considerable water contamination (30 mmol compared to 192 mmol A$_2$PCl), the excess triethylamine provides ample protection for the monophosphite intermediate and avoids significant loss in selectivity, as evidenced by the relatively low cyclophosphite distribution in the samples (maximum 1.6% P as cyclophosphite).

Similarly in Example 31 (Table 17), the water is added and dissolved in the first portion of the bisaryl compound feed. Again, as indicated by the $^{31}$P NMR results in Table 17, over time a similar amount (28 mmol) of acidic phosphorus-containing compound of Structure IXa is formed. However, the transformation to POP is significantly slower and higher levels of the acidic phosphorus-containing compound, presumed to be of Structure XIa, are present during the addition period of the bisaryl compound, as compared to Example 30. Although the same excess of triethylamine was used, about ten times as much of the monophosphite intermediate is converted to cyclophosphite (9.9% of the total phosphorus) compared to the experiments where the water is added before the addition of the bisaryl compound, and this causes a diphosphite selectivity drop from 97% to 85%. While not wishing to be bound by theory, one possible interpretation is that in addition to binding acidic species, triethylamine retards the intramolecular reaction of the monophosphite intermediate by transforming acidic phosphorus-containing compounds, such as those of Structure IXa, into non-acidic POP type structures, thus inhibiting acidic catalysis. If water contamination is occurring from the bisaryl compound feed, the deactivation process to form POP is slower since phosphorochloridite concentrations are low at increasing phosphorochloridite conversion. Free acid is present in higher concentrations over a longer period of time during the bisaryl addition, therefore increasing the observed rate of monophosphite intermediate conversion to cyclophosphite. Maintaining water contamination of the bisaryl compound below 1% and toluene solutions of the bisaryl compound below 0.1%, for example between 0 ppm and 300 ppm water by weight, avoids a significant diphosphite selectivity drop even when 1.4 molar equivalents of triethylamine are used during diphosphite synthesis.

With less excess triethylamine present, the requirements on water contamination are more stringent. In Table 18, some results from Table 14 are supplemented and compared to those from Examples with controlled water contamination from Tables 16 and 17. The experiments with deliberate water contamination but larger excess of triethylamine illustrate the compounds effect of the amount of acidic phosphorus-containing compound of Structure IXa and triethylamine present during the addition of the bisaryl compound. Experiments with higher levels of acidic phosphorus-containing compounds show higher levels of cyclophosphite (Table 18, Examples 31, 24, and 25 as compared to Examples 30, 21, and 22) but excess tertiary organic amine, such as triethylamine, can partially compensate for higher acid (Examples 30 and 31 as compared to Examples 24 and 25). As an estimate derived from Table 18, at triethylamine levels at or below 1.02 molar equivalents triethylamine per equivalent $A_2PCl$, the water contamination of the bisaryl compound feed should be less than 300 ppm water to avoid a significant drop in the diphosphite selectivity during the bisaryl addition phase of the diphosphite synthesis.

Experiments are performed to address the impact of the concentration of reactants in the presence of hydrolysis products on diphosphite selectivity during the addition of the bisaryl compound. Examples 30 and 31 are performed at 20° C., with 1.4 molar equivalents of triethylamine per equivalent of phosphorochloridite, and with the addition of the bisaryl compound made in portions. The distribution of phosphorus species (% P), including the acidic phosphorus-containing compounds represented as "H", is given in Table 19 for Examples 30, 31, and other related Examples. Example 32 is initially run as for Examples 30 and 31 but before adding triethylamine the reactor contents, the reaction mixture is divided into two portions, one being one-fourth the volume (Example 32A) and the other being three-fourths the volume (Example 32B) of the undivided reaction mixture. The one-fourth volume portion remains in the reactor and was diluted with dry toluene to the same volume as the three-fourths volume portion, which is not diluted. After the same molar equivalents of triethylamine are added to the diluted (32A) and undiluted (Example 32B) reaction mixtures, both Example 32A and 32B portions show adventitious hydrolysis of the phosphorochloridite equivalent to about 20 mmol of water, the only difference being that reaction solution concentrations differed by a factor of 3. To both phosphorochloridite solutions of Examples 32A and 32B, the same relative equivalents of 1 M bisaryl compound solution in toluene are added in the same fashion as described in Table 16. Although the amount of moisture intrusion on the more concentrated Example 32B (Table 21) appear to be higher, only 2.4% of the total phosphorus is found as cyclophosphite, whereas the more dilute Example 32A (Table 20) showed 11.1% of the total phosphorus as cyclophosphite. At the same time, higher relative amounts of acidic hydrolysis products are observed under more dilute conditions (Example 32A as compared to Example 32B). The estimated concentrations [H conc. (mmol/Kg)] of acidic phosphorus-containing compounds, based upon $^{31}P$ NMR measurement, are overall very similar.

The results in Table 22 are more dramatic where concentrations in the reaction solution are about one-fourth of the values found for standard conditions. Although these experiments (Table 22, Examples 34-36) show significantly less water contamination and lower levels of acidic phosphorus-containing compounds, the amount of cyclophosphite formed ranges from 20-30% for the faster feed rates (0.23 to 5.1 equivalents per hour) for the bisaryl compound. Surprisingly, the slower and portion-wise bisaryl addition (Table 22, Examples 37-39) result in a significant reduction in cyclophosphite formation, only 5% to 8%, of the total phosphorus.

Experimental Section

Additional experimental details are provided in this section. Unless otherwise noted all experiments are conducted in a standard jacketed baffled 500 mL cylindrical round bottomed glass reactor (ID 5¼"; H=9½) equipped with a three-necked glass cover. The overhead stirrer impeller is shaped as a plus sign (+) formed by two panels attached to a shaft at the cross point (all angles are 90 degree). Each of the two panels is 58 mm long, 20 mm high and 3 mm thick. All solutions of triethylamine, thymol, and 2,4-xylenol in toluene are made in a drybox and stored over molecular sieves. All glassware is heated in an oven overnight and cooled in a drybox antechamber under vacuum and finally flushed with dry $N_2$.

For quantitative NMR analysis, 0.250 mL of the organic layer without tertiary organic amine hydrogen chloride solids and 0.600 mL of a 0.01 molar solution of triphenylphosphine oxide (TPPO) in $C_6D_6$ are combined and analyzed by $^{31}P$ NMR ($T_1$=5 sec.).

Bisaryl compound IIIa may be prepared by any suitable synthetic means known in the art, for example as disclosed in U.S. Patent Application Publication 2003/0100802, in which 2-iso-propyl-4,5-dimethylphenol, is oxidatively coupled in the presence of a molecular oxygen-containing gas and a copper diamine catalyst to provide the desired bisaryl compound.

Preparation of a copper diamine catalyst is described in Tetrahedron Letters, 1994, 35, 7983. A copper halide, such as CuCl, CuBr, CuI, or $CuCl_2$, is added to a mixture of alcohol, such as methanol, and water and the diamine is slowly added. After the addition of the diamine, air is sparged through the mixture with vigorous stirring. The solid catalyst product is filtered. Examples of useful diamines include tetramethylethylenediamine, N,N,N',N'-tetraethyl-1,3-propanediamine, and N,N,N',N'-tetraethylmethane diamine. Alternatively, the catalyst can be prepared in situ by contacting the copper halide and the diamine in the solvent for the coupling reaction.

The oxidative coupling can be carried out by contacting the phenol with a copper complex of a diamine in an inert, preferably aprotic solvent such as dichloromethane, toluene, chlorobenzene, or saturated hydrocarbon, preferably one having a flash-point higher than the reaction temperature, at a temperature between 5° C. and 100° C., for example around 30° C. The product is generally isolated by dilution with a saturated hydrocarbon solvent, filtration, and optionally purified by washing with aqueous mineral acid or a copper-sequestering reagent such as the sodium salt of ethylenediaminetatraacetic acid (EDTA). The product may optionally be purified by recrystallization.

The substituted phenol 2-iso-propyl-4,5-dimethylphenol may be prepared by any suitable synthetic means known in the art, for example by alkylation of thymol or 3,4-xylenol. Houben-Weyl, Vol. 6/1C (pages 955-985), G. Thieme Verlag, Stuttgart 1976, teaches general methods for the alkylation of phenols with alkenes using homogeneous and heterogeneous acid catalysts. U.S. Pat. No. 3,037,052, for example, discloses the use of macroreticular ion exchange resins containing sulfonic acid groups as catalysts for the alkylation of phenols with alkenes.

Example 15 is carried out in a 2 liter baffled, jacketed reactor with overhead stirrer, $N_2$ blanket, and two feed lines from a peristaltic pump. 200 mL of 2.0 M $PCl_3$ solution in toluene is charged into the reactor using a cannula and positive $N_2$ pressure; the solution is cooled to +5° C. Under vigorous stirring, a solution of 202 mL of 2.0 M triethylamine in toluene and a solution of 200 mL of 2.0 M 2,4-xylenol in toluene are added separately and concurrently at a feed rate of 1 mL/minute via a peristaltic pump. The triethylamine feed is delivered below the surface, while the 2,4-xylenol feed is delivered above the surface. During the addition period, the reaction temperature is maintained at about +5° C. A second 200 mL each of 2.0 M triethylamine solution in toluene and 2.0 M 2,4-xylenol solution in toluene are added separately and concurrently via a peristaltic pump at the same feed rate as before. A correction feed of triethylamine solution in toluene and 2,4-xylenol solution in toluene are added as necessary based on $^{31}P$ NMR analysis of the reaction mixture. Quantitative $^{31}P$ NMR analysis of the organic phase is conducted to determine the mol % phosphorochloridite. The reaction is then warmed to 20° C. and the stirring set to 900 rpm; and 200 mL of 2.0 M triethylamine is added at 1 mL/minute. 195 mL of 1.0 M bisaryl compound solution in toluene is then added above the surface at 1.5 mL/minute via peristaltic pump. Reaction workup is to quench with 300 mL of $H_2O$ while stirring vigorously for 10 minutes. The organic layer is separated and washed with 300 mL of 1.0 M aqueous NaOH solution. The organic layer is then washed with 300 mL of saturated brine solution and quantitative $^{31}P$ NMR analysis of the organic phase is conducted.

Example 16 is carried out in a 2 liter baffled, jacketed reactor with overhead stirrer, $N_2$ blanket, and two feed lines from a peristaltic pump. 200 mL of 2.0 M $PCl_3$ solution in toluene is charged into the reactor using a cannula and positive $N_2$ pressure; the solution is cooled to +5° C. Under vigorous stirring, a solution of 200 mL of 4.0 M triethylamine in toluene and a solution of 101 mL of 4.0 M 2,4-xylenol in toluene are added separately and concurrently at a feed rate of 1 mL/minute via a peristaltic pump. The triethylamine feed is delivered below the surface, while the 2,4-xylenol feed is delivered above the surface. During the addition period, the reaction temperature is maintained at about +5° C. A second 200 mL of 4.0 M triethylamine solution in toluene and 101 mL of 4.0 M 2,4-xylenol solution in toluene are added separately and concurrently via a peristaltic pump at the same feed rate as before. A correction feed of triethylamine solution in toluene and 2,4-xylenol solution in toluene are added as necessary based on $^{31}P$ NMR analysis of the reaction mixture. Quantitative $^{31}P$ NMR analysis of the organic phase is conducted to determine the mol % phosphorochloridite. The reaction is then warmed to 20° C. and the stirring set to 900 rpm; and 62 mL of 7.2 M triethylamine was added at 1 mL/minute. 338.5 mL of 0.5 M bisaryl compound solution in toluene was then added above the surface at 0.1 mL/minute via peristaltic pump. Reaction workup was to quench with 300 mL of $H_2O$ while stirring vigorously for 10 minutes. The organic layer was separated and washed with 300 mL of 1.0 M aqueous NaOH solution. The organic layer was then washed with 300 mL of saturated brine solution and quantitative $^{31}P$ NMR analysis of the organic phase was conducted.

For Examples 26-29, the following general procedure was used. Samples of the reaction mixture were analyzed by $^{31}P$ NMR periodically to determine the extent of reaction. In a temperature-controlled 500 mL baffled reactor equipped with an overhead stirrer was charged 200 mL (200 mmol) of 1.0 M $PCl_3$ solution in toluene via $N_2$ pressure and a double-ended needle. Under vigorous stirring, a solution of 100 mL (200 mmol) of 2.0 M triethylamine and a solution of 100 mL (200 mmol) of 2.0 M thymol in toluene are added separately and concurrently via peristaltic pump at 2.22 mL/min. During the addition period the reaction temperature is maintained at 5° C. and the triethylamine is added below the surface while the thymol is added above the surface. Under vigorous stirring, a solution of 100 mL (200 mmol) of 2.0 M triethylamine and a solution of 100 mL (200 mmol) of 2.0 M 2,4-xylenol in toluene are added separately and concurrently via peristaltic pump at 2.22 mL/min. A reaction sample is taken for $^{31}P$ NMR analysis and further details are supplied below for each Example.

For Example 26, the $^{31}P$ NMR analysis indicates that a 3.1% correction of the feed is needed to convert unreacted phosphorodichloridite ($BPCl_2$) to phosphorodichloridites ($ABPCl_2$). 3.1 mL (6.2 mmol) of both the triethylamine and the 2,4-xylenol as solutions in toluene are added separately and concurrently, then 253.8 mmol of triethylamine is added under the surface over approximately 5 minutes. The reaction temperature is cooled to −20° C. A solution of 91 mL (91 mmol, 29.709 g of bisaryl compound) of 1.0 M bisaryl compound is added via peristaltic pump under the conditions given in Table 15. After 100% of the bisaryl compound is added, within 2 minutes another reaction sample was taken. The mixture is stirred over the weekend and sampled again. The stirring is increased to approx. 500 rpm for one hour and sampled. The reaction mixture is washed with 150 mL $H_2O$ and stirred for 5 minutes. After separating the organic phase, it is washed with 150 mL of 1 N aqueous NaOH. After separating the organic phase, it is washed with 150 mL of brine.

For Example 27, 260 mmol of triethylamine is added under the reaction mixture surface over approximately 5 minutes. The reaction temperature is cooled to −20° C. A solution of 91 mL (91 mmol, 29.709 g of bisaryl compound) of 1.0 M bisaryl compound in toluene is added via peristaltic pump under the conditions given in Table 15. After 100% of the bisaryl compound is added, within 2 minutes another reaction sample was taken. The mixture is stirred for three hours and sampled again. The reaction mixture is washed with 150 mL $H_2O$ and stirred for 5 minutes. After separating the organic phase, it is washed with 150 mL of 1 N aqueous NaOH. After separating the organic phase, it is washed with 150 mL of brine. The final organic layer is concentrated by evaporation at 45° C.

For Example 28, 260 mmol of triethylamine is added under the reaction mixture surface over approximately 5 minutes. The reaction temperature is warmed to +20° C. A solution of 93 mL (93 mmol, 30.36 g of bisaryl compound) of 1.0 M bisaryl compound in toluene is added via peristaltic pump under the conditions given in Table 15 over 6 hours. After 100% of the bisaryl compound is added, within 2 minutes another reaction sample is taken. The mixture is stirred over the weekend and sampled again. The reaction mixture is washed with 150 mL $H_2O$ and stirred for 5 minutes. After separating the organic phase, it is washed with 150 mL of 1 N aqueous NaOH. After separating the organic phase, it is washed with 150 mL of brine.

For Example 29, the $^{31}P$ NMR analysis indicated that a 2% correction of the feed is needed and appropriate amounts of triethylamine and xylenol were added. 246 mmol of triethylamine is then added under the reaction mixture surface over approximately 5 minutes. The reaction temperature is warmed to +20° C. A solution of 91 mL (91 mmol, 29.709 g of bisaryl compound) of 1.0 M bisaryl compound in toluene is added via peristaltic pump under the conditions given in Table 15. After 100% of the bisaryl compound is added, within 2 minutes another reaction sample is taken. The mixture is stirred for 1.5 hours and sampled again. The reaction mixture is washed with 150 mL $H_2O$ and stirred for 5 minutes. After separating the organic phase, it is washed with 150 mL of 1 N aqueous NaOH. After separating the organic phase, it is washed with 150 mL of brine. The final organic layer is concentrated by evaporation at 45° C.

Example 30 is performed as follows, with the 2 M triethylamine solution, the 2 M 2,4-xylenol solution, and the solution of bisaryl compound being prepared in the drybox and dried over sieves prior to their use. Samples of the reaction mixture are analyzed by $^{31}P$ NMR periodically to determine the extent of reaction. In a temperature-controlled 500 mL baffled reactor equipped with an overhead stirrer is charged 200 mL (200 mmol) of 1.0 M $PCl_3$ in toluene via $N_2$ pressure and a double-ended needle. Under vigorous stirring, a solution of 100 mL (200 mmol) of 2.0 M triethylamine and a solution of 100 mL (200 mmol) of 2.0 M 2,4-xylenol in toluene are added separately and concurrently via peristaltic pump at 2.22 mL/min. During the addition period the reaction temperature was maintained at 5° C. and the triethylamine is added below the surface while the 2,4-xylenol is added above the surface. Under vigorous stirring, a solution of 100 mL (200 mmol) of 2.0 M triethylamine and a solution of 100 mL (200 mmol) of 2.0 M 2,4-xylenol in toluene are added separately and concurrently via peristaltic pump at 2.22 mL/min. At this point, 30 mmol of water is added and the mixture stirred for 30 minutes. Triethylamine (260 mmol) is added under the surface of the reaction mixture over approximately 5 minutes. The reaction mixture is warmed to +20° C. and a solution of 65 g (71.7 mmol, 23.4 g of bisaryl compound) of 1.0 M bisaryl compound IIIa is added via peristaltic pump intermittently, under 480 rpm stirring. 40 g of this 1.0 M bisaryl compound solution is added over 2 hours, then 20 g more is added over 4 hours and the mixture stirred overnight. An additional 5 g of this 1.0 M bisaryl compound solution is added over 2 hours. The reaction mixture is then washed with 150 mL of water and stirred for 5 minutes. After separating the organic phase, it is washed with 150 mL of 1 M aqueous NaOH. After separating the organic phase, it is washed with 150 mL of brine.

Example 31 is performed as for Example 30, except that no water is added to the reaction mixture prior to warming to +20° C. Instead, 30 mmol of water is added to the solution of 65 g (71.7 mmol, 23.4 g of bisaryl compound) of 1.0 molar bisaryl compound IIIa, which is added intermittently via a peristaltic pump.

Example 32A is performed as for Example 30 through the separate and concurrent additions of triethylamine and 2,4-xylenol. At that point it is determined by $^{31}P$ NMR analysis that a 3% feed correction of triethylamine and 2,4-xylenol is needed, and this feed correction is made. Approximately three-quarter of the reaction mixture is then removed using a cannula and transferred to a dried one-liter container, where the mixture is stored in a freezer (to be used in Example 32B, see below). The mixture remaining in the reactor is sampled for $^{31}P$ NMR analysis, then diluted with dry toluene back to the same volume as before the removal by cannula. Triethylamine (65 mmol) is added under the reaction surface over approximately five minutes; the mixture became light brown on stirring. The reaction mixture is warmed to +20° C. and a 13.4 g (14.8 mmol, 4.82 g of bisaryl compound) of 1.0 M bisaryl compound IIIa solution in toluene was added intermittently via peristaltic pump under 480 rpm stirring. 8.4 g of this 1.0 M bisaryl compound solution is added over 2 hours, with 5 g more added over 2 hours. The reaction mixture is washed with 75 mL of water and stirred for 5 minutes. After separating the organic phase, it is washed with 75 mL of 1 M aqueous NaOH. After separating the organic phase, it is washed with 75 mL of brine.

For Example 32B, the solution is removed via cannula from Example 32A and stored in the freezer was charged via cannula under $N_2$ to a temperature-controlled 500 mL baffled reactor equipped with an overhead stirrer. Triethylamine (195 mmol) is added under the surface of the reaction mixture over approximately 5 minutes. The reaction mixture is then warmed to +20° C. and 31 g (34.2 mmol, 11.2 g of bisaryl compound) of a 1.0 M bisaryl compound IIIa solution is added intermittently under 480 rpm stirring. 26 g of the 1.0 M bisaryl compound solution is added over 2 hours, with 5 additional grams added over 2 hours, at which point the mixture is allowed to stir for 2 hours. The reaction mixture is then washed with 150 mL water and stirred for 5 minutes. Work-up is as for Example 32A.

For Examples 34-39, the following general procedure is used. Samples of the reaction mixture are analyzed by $^{31}P$ NMR periodically to determine the extent of reaction. In a temperature-controlled 500 mL baffled reactor equipped with an overhead stirrer is charged 200 mL (50 mmol) of 0.25 M $PCl_3$ solution in toluene via $N_2$ pressure and a double-ended needle. Under vigorous stirring, a 100 mL (50 mmol) of 0.5 M triethylamine solution in toluene and a 100 mL (50 mmol) of 2,4-xylenol solution in toluene is added separately and concurrently via peristaltic pump at 2.2 mL/min. During the addition period the reaction temperature is maintained at 5° C. and the triethylamine is added below the surface of the reaction mixture while the 2,4-xylenol is added above the surface. Under vigorous stirring, a 100 mL (50 mmol) of 0.5 M triethylamine solution in toluene and a 100 mL (50 mmol) of 0.5 M 2,4-xylenol solution are added separately and concurrently via peristaltic pump at 2.22 mL/min. 65 mmol of triethylamine is then added under the surface over approximately 5 minutes. The reaction temperature is cooled to −20° C. and 93 mL (23.3 mmol, 7.607 of bisaryl compound) of 0.25 M bisaryl compound IIIa solution is added via peristaltic pump under 270 rpm stirring. After all the bisaryl compound is added, the reaction mixture is stirred for 3 hours. The reaction mixture is washed with 75 mL water and stirred for 5 minutes. After separating the organic phase, it is washed with 75 mL of 1 M aqueous NaOH. After separating the organic phase, it is washed with brine.

For Example 35, the $^{31}P$ NMR analysis indicates that a 3.3% correction of the feed (both triethylamine and 2,4-xylenol) is needed, and the additions are made. 63.5 mmol of triethylamine is then added under the surface over approximately 5 minutes. Instead of cooling the reaction mixture, the reaction mixture is warmed to +20° C. 91 mL (22.75 mmol, 7.427 of bisaryl compound) of 0.25 M bisaryl compound IIIa solution is added as for Example 34. After this bisaryl compound is added, the reaction mixture is stirred for 2 hours, sampled, then allowed to stir over the weekend. The reaction mixture is worked up as for Example 34. The final organic layer is evaporated at 45° C. and pumped down under vacuum overnight. 22.2 g of a sticky yellow solid is obtained.

For Example 36, the general procedure of Example 35 is followed. A 2.3% correction to the feed is made. After addition of 64 mmol of triethylamine and warming to +20° C., 93 mL (23.25 mmol, 7.59 g of bisaryl compound) of 0.25 M bisaryl compound IIIa solution is added with 480 rpm stirring over 4 hours. After bisaryl compound addition is complete, the reaction mixture is stirred overnight and then worked up as for Example 34. The final organic layer is evaporated at 45° C. and pumped down under vacuum overnight. 21.8 g of a sticky yellow solid is obtained.

For Example 37, the general procedure of Example 35 is followed. No correction to the feed is necessary. The reaction mixture is warmed to +20° C. 72.49 g (20.79 mmol, 6.79 g of bisaryl compound) of a 0.25 M bisaryl compound IIIa solution in toluene is added intermittently under 480 rpm stirring. 29 g of this 0.25 M bisaryl compound solution is added over 2 hours and 10 minutes; the reaction mixture is stirred for an additional 18 hours. 20 g more of this 0.25 M bisaryl compound solution is added over 4 hours and the mixture stirred overnight, then over the weekend. 10 g more of this 0.25 M bisaryl compound solution is added over 2.5 hours, and the mixture stirred overnight. 5 g more of this 0.25 M bisaryl compound solution is added over 1 hour, and the remainder of this solution is added over 2 hours.

For Example 38, the reaction solutions are prepared in the drybox and the 0.5 M triethylamine (100 mmol) solution in toluene, the 2,4-xylenol solution in toluene, and the bisaryl compound solution in toluene are dried over sieves for 3 days prior to their use in the synthesis reaction. The general procedure of Example 35 is followed. After the concurrent and separate addition of 2,4-xylenol and triethylamine, a 3.3% correction of the triethylamine and 2,4-xylenol is made. 64.35 mmol of triethylamine is then added over approximately 5 minutes, under the surface of the solution. The reaction mixture is warmed to +20° C. 75 g (21.5 mmol, 7.023 g of bisaryl compound) of a 0.25 M bisaryl compound Ma solution in toluene is added intermittently via peristaltic pump under 480 rpm stirring. 40 g of this 0.25 M bisaryl compound solution is added over 2 hours and 20 minutes, 20 g more of this 0.25 M bisaryl compound solution is added over 4 hours and the mixture stirred overnight. 5 g more of this 0.25 M bisaryl compound solution is added over 2 hours and the mixture stirred overnight. Then 5 g more of this 0.25 M bisaryl compound solution is added over 2 hours, and an additional 5 g of this 0.25 M bisaryl compound solution is added over 2 hours. The reaction mixture is worked up as for Example 34.

For Example 39, the reaction solutions are prepared in the drybox and the 0.5 M triethylamine (100 mmol) solution in toluene, the 2,4-xylenol solution in toluene, and the bisaryl compound solution in toluene are dried over sieves for 3 days prior to their use in the synthesis reaction. The general procedure of Example 35 is followed. After the concurrent and separate addition of 2,4-xylenol and triethylamine, a 1.0% feed correction is made for Example 39. 65.5 mmol of triethylamine is then added over approximately 5 minutes, under the surface of the solution. The reaction mixture is warmed to +20° C. 70 g (20.1 mmol, 6.55 g of bisaryl compound) of a 0.25 M bisaryl compound IIIa solution in toluene is added intermittently via peristaltic pump under 480 rpm stirring. 40 g of this 0.25 M bisaryl compound solution is added over 2 hours, then 20 g more of this 0.25 M bisaryl compound solution is added over 4 hours and the mixture stirred overnight. An additional 5 g of this 0.25 M bisaryl compound solution is added over 2 hours, then 5 g more of this solution is added over 2 hours, with an additional 5 g of this solution is then added over 2 hours. At this point, 1.23 g of triethylamine is added, and the reaction mixture is stirred for 2 hours.

Example 40

Temperature Study at 55° C.

The phosphorochloridite of 2,4-xylenol, $A_2PCl$ wherein A is 2,4-dimethylphenoxide, is synthesized following a method disclosed in WO2004/050588 to produce a 0.34 M phosphorochloridite solution (89% $A_2PCl$, 2% $APCl_2$, 8% $A_3P$) in toluene.

With respect to the phosphorochloridite, about 1.3 molar equivalents of dry triethylamine are added to the reaction flask containing the 0.34 M phosphorochloridite solution then the resulting mixture is heated to about 55° C. With mechanical stirring of the reaction mixture over a period of about 2 hours, a 1 M solution of the bisaryl compound IIIa in toluene is added to the reaction flask at a reaction mixture temperature of about 55° C. The total amount of bisaryl compound to be fed was predetermined and calculated to allow for 100% conversion of phosphorochloridite at the final stage of the reaction. The distributions to phosphorus species are derived from $^{31}P$ NMR measurements and are listed in Table 23.

Example 41

Temperature Study at 35° C.

The phosphorochloridite of 2,4-xylenol, $A_2PCl$ wherein A is 2,4-dimethylphenoxide, is synthesized following a method disclosed in WO2004/050588 to produce a 0.35 M phosphorochloridite solution (89% $A_2PCl$, 1% $APCl_2$, 9% $A_3P$) in toluene.

Example 40 is repeated with this 0.35 M phosphorochloridite solution and 1.3 molar equivalents of triethylamine. An exception being that the temperature of the reaction mixture during the addition of the 1 M solution of bisaryl compound is 35° C. The distributions to phosphorus species are derived from $^{31}P$ NMR measurements and are listed in Table 24.

Example 42

Temperature Study at 15° C.

The phosphorochloridite of 2,4-xylenol, $A_2PCl$ wherein A is 2,4-dimethylphenoxide, is synthesized following a method disclosed in WO2004/050588 to produce a 0.34 M phosphorochloridite solution (87% $A_2PCl$, 2% $APCl_2$, 10% $A_3P$) in toluene.

Example 40 is repeated with this 0.4 M phosphorochloridite solution and 1.2 molar equivalents of triethylamine. An exception being that the temperature of the reaction mixture during the addition of a 0.6 M solution of bisaryl compound is 15° C. The distributions to phosphorus species are derived from $^{31}P$ NMR measurements and are listed in Table 25.

Example 43

Temperature Study at 10° C.

The phosphorochloridite of 2-4-xylenol, $A_2PCl$ wherein A is 2,4-dimethylphenoxide, is synthesized following a method disclosed in WO2004/050588 to produce a 0.4 M phosphorochloridite solution (85% $A_2PCl$, 4% $APCl_2$, 11% $A_3P$) in toluene.

Example 40 is repeated with this 0.4 M phosphorochloridite solution and 1.2 molar equivalents of triethylamine, but for Example 43, the temperature of the reaction mixture during the addition of a 0.6 M solution of bisaryl compound is 10° C. The distributions to phosphorus species are derived from $^{31}P$ NMR measurements and are listed in Table 26.

The temperature study of Examples 40-43 show that a selectivity to diphosphite Ia from the bisaryl compound by the present method does not decrease as the temperature is increased.

Example 44

Hydrocarbon Solvent Study

In some Examples above, the reaction mixture further comprises toluene as the aromatic hydrocarbon solvent. In Example 44, the toluene of Example 40 is replaced with a saturated hydrocarbon solvent, cyclohexane. That is, the phosphorochloridite of 2,4-xylenol is synthesized in cyclohexane following a method disclosed in WO2004/050588 and the bisaryl compound IIIa dissolved in cyclohexane is feed to this phosphorochloridite in the presence of triethylamine to produce diphosphite Ia. In comparison to the aromatic hydrocarbon solvent at the same stirrer rpm speed, the triethylamine hydrogen chloride solids precipitated from the reaction mixture comprising cyclohexane are more difficult to stir.

Examples of Embodiments

The following are additional examples of embodiments of the disclosed method.

Example 45

A diphosphite of Structure I is produced,

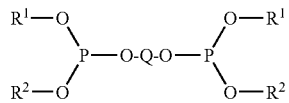

Structure I comprising the steps of:
contacting a phosphorochloridite of Structure II,

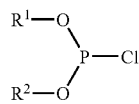

Structure II with a bisaryl compound selected from the group consisting of Structure III, Structure IV, and Structure V,

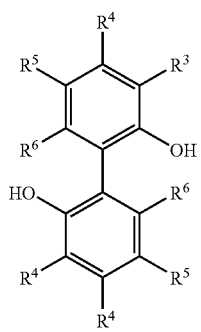

Structure III

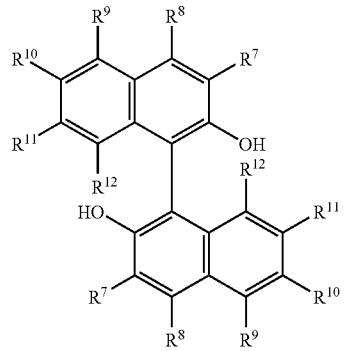

Structure IV

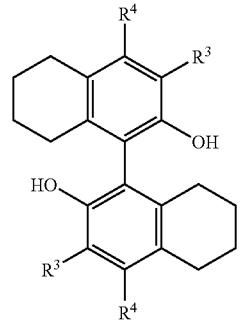

Structure V and a tertiary organic amine, comprising a basic nitrogen atom or a plurality of nitrogen atoms, to produce a reaction mixture comprising a diphosphite of Structure I;

wherein,
the contacting is done by at least one contacting method selected from the group consisting of,
(i). feeding the bisaryl compound to a mixture of phosphorochloridite and tertiary organic amine, and
(ii). feeding the bisaryl compound and the tertiary organic amine either separately or as a mixture to the phosphorochloridite;
and the contacting is done by controlling the feeding such that:
a first mole ratio is at least 2.0 during all stages of the contacting, wherein the first mole ratio is defined as moles of phosphorochloridite in the reaction mixture divided by moles of bisaryl compound fed to the reaction mixture, and
a second mole ratio is at least 1.0 during all stages of the contacting, wherein the second mole ratio is defined as moles of basic nitrogen atoms from the tertiary organic amine fed to the reaction mixture divided by moles of phosphorochloridite in the reaction mixture; and
the method is characterized in that the contacting occurs at a temperature from about 10° C. to about 110° C. to produce the diphosphite in the reaction mixture with a selectivity between 70% and 100% from the bisaryl compound;
wherein,
the selectivity equals moles of diphosphite produced in the reaction mixture divided by total moles of the bisaryl compound contacting the phosphorochloridite;

wherein in Structures I to V,
R$^1$ and R$^2$ are the same or different, substituted or unsubstituted, monovalent aryl groups; each of R$^3$, R$^4$, R$^5$, R$^6$, R$^7$, R$^8$, R$^9$, R$^{10}$, R$^{11}$, and R$^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogenyl groups; and O-Q-O is a dianion of the bisaryl compound.

Example 46

Example 45 is repeated wherein the reaction mixture further comprises at least one aromatic hydrocarbon solvent.

Example 47

Example 45 is repeated further comprising controlling the feeding such that the first mole ratio is between 2.1 to 2.7 during the stage of the contacting wherein phosphorochloridite conversion is between 90% and 100%.

Example 48

Example 45 is repeated further comprising controlling the feeding such that a phosphorochloridite concentration is greater than or equal to 0.02 moles per liter in the reaction mixture during the stage of the contacting wherein phosphorochloridite conversion is from 0% to 90%.

Example 49

Example 48 is repeated wherein the phosphorochloridite concentration is between 0.02 and 2.0 moles per liter in the reaction mixture during the stage of the contacting wherein phosphorochloridite conversion is from 0% to 90%.

Example 50

Example 45 is repeated further comprising controlling the second mole ratio from 1.0 to 1.5 during any stage of the contacting.

Example 51

Example 45 is repeated further comprising feeding the bisaryl compound to the phosphorochloridite at a feed rate between 0.04 and 10 molar equivalents per hour, relative to total moles of phosphorochloridite undergoing the contacting.

Example 52

Example 45 is repeated further comprising feeding the bisaryl compound to the phosphorochloridite as a bisaryl solution comprising the bisaryl compound and hydrocarbon solvent.

Example 53

Example 52 is repeated wherein the reaction mixture further comprises an upper liquid surface, the contacting further comprises providing a stirring shaft comprising at least one impeller attached to the stirring shaft wherein at least one impeller is located below the upper liquid surface, and the feeding further comprises providing rotational energy to the stirring shaft to mechanically stir the reaction mixture.

Example 54

Example 53 is repeated further comprising feeding the bisaryl solution to the phosphorochloridite by at least one mixing method selected from the group consisting of,
feeding the bisaryl compound to the reaction mixture above the upper liquid surface by flowing the bisaryl solution through at least one liquid distributor that disperses the bisaryl solution over at least a portion of the upper surface;
feeding the bisaryl compound to the reaction mixture above the upper liquid surface by flowing the bisaryl solution through at least one liquid distributor that disperses the bisaryl solution over at least a portion of the upper surface and feeding the tertiary organic amine to the reaction mixture below the upper liquid surface;
feeding the bisaryl compound to the reaction mixture by flowing the bisaryl solution through at least one feed line that directs the bisaryl solution toward an impeller located below the upper liquid surface;
feeding the bisaryl compound to the reaction mixture by flowing the bisaryl solution through at least one feed line that directs the bisaryl solution toward an impeller located below the upper liquid surface and feeding the tertiary organic amine to the reaction mixture by flowing the tertiary organic amine through at least one feed line that directs the tertiary organic amine toward an impeller located below the upper liquid surface; and
the bisaryl solution further comprises at least a portion of the tertiary organic amine fed to the reaction mixture and feeding the bisaryl compound to the reaction mixture by flowing the bisaryl solution, further comprising the tertiary organic amine, through at least one feed line that directs the bisaryl solution toward an impeller located below the upper liquid surface.

Example 55

Example 45 is repeated wherein the bisaryl compound, the tertiary organic amine, or a combination of the bisaryl compound and the tertiary organic amine, contacting the phosphorochloridite further comprise a total of from 0 ppm to 300 ppm by weight of water.

Example 56

Example 45 is repeated further comprising precipitating a tertiary organic amine hydrogen chloride salt from the reaction mixture during the contacting.

Example 57

Example 45 is repeated further comprising producing at least one phosphorus-containing co-product in the reaction mixture selected from the group consisting of P(OR$^1$)(OR$^2$)$_2$, P(OR$^1$)$_2$(OR$^2$), P(OR$^1$)$_3$, P(OR$^2$)$_3$, a compound of Structure VIa, and a compound of Structure VIb,

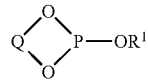

Structure VIa

-continued

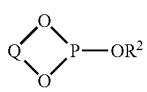

Structure VIb wherein, less than 30% of the total phosphorus in the reaction mixture is in the form of the at least one phosphorus-containing co-product produced from the contacting.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Many aspects and embodiments have been described above and are merely exemplary and not limiting. After reading this specification, skilled artisans appreciate that other aspects and embodiments are possible without departing from the scope of the invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any sub-combination. Further, reference to values stated in ranges includes each and every value within that range.

TABLE 3

Distributions [% Phosphorus (% P)] of Major Products and Intermediates, as Derived from $^{31}P$ NMR Measurements, and Diphosphite Selectivity During the Synthesis of Diphosphite Ia Using Different Feed Addition Modes.

| Example | % Feed[a] Portion Added | $A_2PCl$[b] (% P) | Cyclophosphite (% P) | Monophosphite (% P) | Diphosphite (% P) | Triphosphite (% P) | POP (% P) | H (% P) | SEL (%) |
|---|---|---|---|---|---|---|---|---|---|
| 1* | 62 | 2.3 | 0.9 | 0.0 | 87.0 | 9.8 | 0.0 | 0.0 | 99.0 |
|  | 100 | 3.4 | 1.1 | 0.9 | 84.1 | 9.8 | 0.6 | 0.0 | 97.7 |
|  | 25° C. | 0.0 | 1.2 | 0.0 | 87.2 | 9.4 | 2.2 | 0.0 | 98.7 |
| 1b | 42 | 6.9 | 2.0 | 5.6 | 75.4 | 10.1 | 0.0 | 0.0 | 90.9 |
|  | 100 | 2.5 | 1.5 | 1.0 | 83.9 | 10.5 | 0.5 | 0.0 | 97.1 |
|  | 25° C. | 0.0 | 1.7 | 0.0 | 85.6 | 10.4 | 2.4 | 0.0 | 98.1 |
| 2 | 23 | 57.5 | 1.9 | 27.4 | 4.1 | 9.1 | 0.0 | 0.0 | 12.2 |
|  | 46 | 19.7 | 0.0 | 30.6 | 27.8 | 18.1 | 0.0 | 3.7 | 47.7 |
|  | 68 | 5.8 | 7.6 | 2.0 | 67.6 | 12.5 | 0.0 | 4.4 | 87.5 |
|  | 100 | 0.0 | 2.1 | 1.3 | 80.4 | 10.6 | 1.4 | 4.2 | 95.9 |
|  | 25° C. | 1.1 | 1.4 | 0.0 | 85.5 | 10.3 | 1.6 | 0.0 | 98.3 |
| 3 | 23 | 69.7 | 0.5 | 0.7 | 19.7 | 9.4 | 0.0 | 0.0 | 94.1 |
|  | 46 | 48.1 | 0.7 | 1.2 | 39.9 | 10.1 | 0.0 | 0.0 | 95.4 |
|  | 68 | 29.5 | 0.8 | 0.8 | 58.5 | 9.9 | 0.0 | 0.4 | 97.3 |
|  | 100% | 7.7 | 1.1 | 3.3 | 77.9 | 10.0 | 0.0 | 0.0 | 94.7 |
|  | 25° C. | 3.4 | 1.1 | 0.0 | 84.6 | 9.8 | 1.1 | 0.0 | 98.7 |
| 4 | 23 | 0.0 | 7.7 | 75.0 | 5.2 | 12.1 | 0.0 | 0.0 | 5.9 |
|  | 46 | 0.0 | 8.6 | 59.6 | 18.9 | 12.9 | 0.0 | 0.0 | 21.7 |
|  | 68 | 0.0 | 5.3 | 34.6 | 45.7 | 14.4 | 0.0 | 0.0 | 53.4 |
|  | 100 | 2.9 | 3.7 | 5.4 | 74.6 | 13.4 | 0.0 | 0.0 | 89.1 |
|  | 25° C. | 0.0 | 3.9 | 1.1 | 82.0 | 13.0 | 0.0 | 0.0 | 94.2 |
| 5 | 23 | 67 | 0 | 0 | 24 | 9 | 0 | 0 | 100 |
|  | 46 | 46 | 0 | 0 | 45 | 9 | 0 | 0 | 100 |
|  | 68 | 29 | 1 | 1 | 60 | 9 | 0 | 0 | 97.1 |
|  | 100 | 7 | 1 | 4 | 79 | 10 | 0 | 0 | 94.4 |
|  | 25° C. | 2 | 1 | 0 | 87 | 10 | 0 | 0 | 98.9 |
| 6 | 23 | 0 | 5 | 77 | 8 | 10 | 0 | 0 | 8.9 |
|  | 46 | 2 | 4 | 61 | 22 | 11 | 0 | 0 | 25.7 |
|  | 68 | 0 | 2 | 22 | 66 | 10 | 0 | 0 | 72.9 |
|  | 100 | 7 | 2 | 15 | 66 | 10 | 0 | 0 | 79.4 |
|  | 25° C. | 0 | 3 | 4 | 81 | 10 | 1 | 1 | 92.2 |

[a]Percent of total bisaryl compound fed to the phosphorochloridite;
[b]A is 2,4-dimethylphenoxide.

TABLE 4

Relative Concentrations (Rel. Conc.) of Cyclophosphite VIIa, Monophosphite VIa, and Acidic Phosphorus-Containing Species H in the Presence and Absence of Phosphorochloridite IIa and/or Triethylamine.

| Example | Time (min.) | Cyclophosphite Rel. Conc. (%) | Monophosphite Rel. Conc. (%) | H Rel. Conc. (%) | Monophosphite Equiv. Added | Phosphorochloridite Equiv. Added | $H_2O$ Equiv. Added | $NEt_3$ Equiv. Added |
|---|---|---|---|---|---|---|---|---|
| 7 | 0 | 4 | 96 | ~25 | 1 | 1 | ~11 | 6.6 |
| 8 | 16 | 40 | 60 | ~25 | 1 | 1 | ~11 | 6.6 |

TABLE 4-continued

Relative Concentrations (Rel. Conc.) of Cyclophosphite VIIa, Monophosphite VIa, and Acidic Phosphorus-Containing Species H in the Presence and Absence of Phosphorochloridite IIa and/or Triethylamine.

| Example | Time (min.) | Cyclophosphite Rel. Conc. (%) | Monophosphite Rel. Conc. (%) | H Rel. Conc. (%) | Monophosphite Equiv. Added | Phosphorochloridite Equiv. Added | $H_2O$ Equiv. Added | $NEt_3$ Equiv. Added |
|---|---|---|---|---|---|---|---|---|
| 9  | 120 | 58 | 42 | ~25 | 1 | 1 | ~11 | 6.6 |
| 10 | 300 | 94 | 6  | ~25 | 1 | 1 | ~11 | 6.6 |
| 11 | 21  | 10 | 90 |     | 1 | — | ~11 | —   |
| 12 | 21  | 11 | 89 |     | 1 | — | ~11 | 6.6 |
| 13 | 10  | 99 |    | ~25 | 1 | 1 | ~11 | —   |

TABLE 6

Distribution [% Phosphorus (% P)] of Phosphorus Species, as Derived from $^{31}$P NMR Measurements, During Bisaryl Addition to Phosphorochloridite for the Synthesis of Diphosphite Ia Under Dilute Conditions (0.057 M Phosphorochloridite Starting Concentration).

| | $PCl_3$ (% P) | $APCl_2$ (% P) | $A_2PCl$ (% P) | Cyclophosphite (% P) | Monophosphite (% P) | Diphosphite (% P) | Triphosphite (% P) | POP (% P) | H (% P) | % Bisaryl Added[a] | $A_2PCl$ (M)[b] |
|---|---|---|---|---|---|---|---|---|---|---|---|
| $A_2PCl$ Solution Equiv. OH Added[c] | 0.0 | 0.0 | 95.0 | 0.0 | 0.0 | 0.0 | 5.0 | 0.0 | 0.0 | 0.0 | 0.0576 |
| 0.56 | 0.0 | 0.0 | 37.0 | 2.5 | 14.0 | 38.0 | 7.5 | 1.0 | 0.0 | 56.3 | 0.0230 |
| 0.56 | 0.0 | 0.0 | 26.0 | 1.4 | 1.4  | 64.6 | 6.5 | 1.0 | 0.0 | 56.3 | 0.0164 |
| 0.65 | 0.0 | 0.0 | 20.7 | 1.3 | 3.2  | 67.2 | 6.0 | 1.6 | 0.0 | 65.4 | 0.0135 |
| 0.75 | 0.0 | 0.0 | 15.6 | 1.5 | 6.2  | 67.9 | 6.6 | 2.3 | 0.0 | 74.6 | 0.0109 |
| 0.84 | 0.0 | 0.0 | 8.2  | 1.7 | 7.5  | 74.3 | 6.4 | 2.0 | 0.0 | 83.8 | 0.0062 |
| 0.84 | 0.0 | 0.0 | 6.1  | 1.8 | 7.1  | 76.4 | 7.0 | 1.6 | 0.0 | 83.8 | 0.0047 |
| 0.84 | 0.0 | 0.0 | 1.6  | 1.6 | 3.1  | 81.6 | 8.1 | 2.3 | 1.7 | 83.8 | 0.0034 |
| 0.88 | 0.0 | 0.0 | 0.0  | 2.4 | 1.5  | 85.1 | 6.9 | 3.2 | 1.5 | 88.3 | 0.0029 |
| 0.88 | 0.0 | 0.0 | 0.0  | 2.0 | 1.2  | 85.5 | 6.6 | 3.0 | 1.7 | 88.3 | 0.0029 |
| 0.88 | 0.0 | 0.0 | 0.0  | 3.2 | 0.0  | 85.8 | 7.8 | 2.8 | 1.4 | 88.3 | 0.0026 |

[a]Percent of total bisaryl compound IIIa added to the reaction mixture;
[b]Measured $A_2PCl$ molar concentration within the reaction mixture by $^{31}$P NMR;
[c]Molar equivalents of OH groups from the bisaryl compound IIIa added to the reaction mixture relative to total moles of phosphorochloridite, $A_2PCl$, charged to the reaction flask; A is 2,4-dimethylphenoxide.

TABLE 7

Differential Conversion of Phosphorus Species During Bisaryl Addition for the Synthesis of Diphosphite Under Dilute Conditions as Derived from $^{31}$P NMR Measurements. In the Table, Δ Indicates Change From the Previous Entry.

| Equiv. OH Added[c] | $A_2PCl$[a] Δ (mmol) | Cyclophosphite Δ (mmol) | Monophosphite Δ (mmol) | Diphosphite Δ (mmol) | Triphosphite Δ (mmol) | POP Δ (mmol) | H Δ (mmol) | P Balance (mmol) |
|---|---|---|---|---|---|---|---|---|
| 0.56 | −2.78 | 0.12  | 0.67  | 1.82 | 0.12  | 0.05  | 0.00  | 0.00 |
| 0.56 | −0.53 | −0.05 | −0.60 | 1.28 | −0.05 | 0.00  | 0.00  | 0.04 |
| 0.65 | −0.25 | 0.00  | 0.09  | 0.12 | −0.02 | 0.03  | 0.00  | −0.04 |
| 0.75 | −0.24 | 0.01  | 0.14  | 0.03 | 0.03  | 0.03  | 0.00  | 0.00 |
| 0.84 | −0.36 | 0.01  | 0.06  | 0.31 | −0.01 | −0.01 | 0.00  | 0.00 |
| 0.84 | −0.10 | 0.00  | −0.02 | 0.10 | 0.03  | −0.02 | 0.00  | 0.00 |
| 0.84 | −0.22 | −0.01 | −0.19 | 0.25 | 0.05  | 0.03  | 0.08  | 0.00 |
| 0.88 | −0.08 | 0.04  | −0.08 | 0.17 | −0.06 | 0.04  | −0.01 | 0.03 |
| 0.88 | 0.00  | −0.02 | −0.01 | 0.02 | −0.01 | −0.01 | 0.01  | −0.03 |
| 0.88 | 0.00  | 0.06  | −0.06 | 0.01 | 0.06  | −0.01 | −0.01 | 0.05 |

[a]A is 2,4-dimethylphenoxide;
[c]Molar equivalents of OH groups from the bisaryl compound IIIa added to the reaction mixture relative to total moles of phosphorochloridite, $A_2PCl$, charged to the reaction flask

TABLE 8

Distribution [% Phosphorus (% P)] of Phosphorus Species, as Derived from $^{31}$P NMR Measurements, During Bisaryl Addition to Phosphorochloridite for the Synthesis of Diphosphite Ia Under Non-Dilute, Non-Concentrated Conditions (0.27 M Phosphorochloridite Starting Concentration).

| | $PCl_3$ (% P) | $APCl_2$ (% P) | $A_2PCl$ (% P) | Cyclophosphite (% P) | Monophosphite (% P) | Diphosphite (% P) | Triphosphite (% P) | POP (% P) | H (% P) | % Bisaryl Added[a] | $A_2PCl$ (M)[b] |
|---|---|---|---|---|---|---|---|---|---|---|---|
| $A_2PCl$ Solution | 0 | 0 | 95 | 0 | 0 | 0 | 5 | 0 | 0 | 0 | 0.271 |

TABLE 8-continued

Distribution [% Phosphorus (% P)] of Phosphorus Species, as Derived from $^{31}$P NMR Measurements, During Bisaryl Addition to Phosphorochloridite for the Synthesis of Diphosphite Ia Under Non-Dilute, Non-Concentrated Conditions (0.27 M Phosphorochloridite Starting Concentration).

| | PCl$_3$ (% P) | APCl$_2$ (% P) | A$_2$PCl (% P) | Cyclophosphite (% P) | Monophosphite (% P) | Diphosphite (% P) | Triphosphite (% P) | POP (% P) | H (% P) | % Bisaryl Added$^a$ | A$_2$PCl (M)$^b$ |
|---|---|---|---|---|---|---|---|---|---|---|---|
| Equiv. OH Added$^c$ | | | | | | | | | | | |
| 0.49 | 0 | 0 | 18 | 0.0 | 0 | 54.0 | 5.0 | 20 | 4 | 49 | 0.111 |
| 0.85 | 0 | 0 | 0 | 2.2 | 2.6 | 74.7 | 7.2 | 0 | 13 | 85 | 0.034 |
| 0.98 | 0 | 0 | 0 | 2.3 | 2.9 | 87.6 | 7.2 | 0 | 0 | 98 | 0.00 |
| 0.98 | 0 | 0 | 0 | 5.0 | 0 | 86.0 | 9.0 | 0 | 0 | 98 | 0.00 |

$^a$Percent of total bisaryl compound IIIa added to the reaction mixture;
$^b$Measured A$_2$PCl molar concentration within the reaction mixture by $^{31}$P NMR;
$^c$Molar equivalents of OH groups from the bisaryl compound IIIa added to the reaction mixture relative to total moles of phosphorochloridite, A$_2$PCl, charged to the reaction flask; A is 2,4-dimethylphenoxide.

TABLE 9

Mass Balance for the Bisaryl Addition to Phosphorochloridite Under Non-Dilute, Non-Concentrated Conditions (0.27 M Phosphorochloridite Starting Concentration).

| Bisaryl Added Equiv. of Theory | OH Added$^a$ [mmol] | A$_2$PCl$^b$ [mmol] | Cyclophosphite [mmol] | Monophosphite [mmol] | Diphosphite [mmol] | Triphosphite [mmol] | Bisaryl in vs out [mmol] | A$_2$PCl$^b$ Conversion |
|---|---|---|---|---|---|---|---|---|
| — | — | 380 | 0 | 0 | 0 | 20 | 0.0 | 0% |
| 50% | 189 | 166 | 0 | 0 | 216 | 20 | −26.8 | 59% |
| 87% | 331 | 52.8 | 8.8 | 10.4 | 299 | 28.8 | 13.3 | 88% |
| 100% | 380 | 0 | 9.2 | 11.6 | 350 | 28.8 | 9.4 | 100% |
| 100% | 380 | 0 | 20 | 0 | 344 | 36 | 16.6 | 100% |

$^a$Total mmoles of OH groups from the bisaryl compound added to the reaction mixture;
$^b$A is 2,4-dimethylphenoxide.

TABLE 10

Differential Conversion of Phosphorus Species, as Derived from $^{31}$P NMR Measurements, During Bisaryl Addition for the Synthesis of Diphosphite Ia Under Non-Dilute, Non-Concentrated Conditions. In the Table, Δ Indicates Change From the Previous Entry.

| Bisaryl Added Equiv. | OH Added$^a$ Δ [mmol] | A$_2$PCl Δ [mmol] | Cyclophosphite Δ [mmol] | Monophosphite Δ [mmol] | Diphosphite Δ [mmol] | Triphosphite Δ [mmol] | Bisaryl Balance [mmol] | P Balance [mmol] | A$_2$PCl Conc. (M) |
|---|---|---|---|---|---|---|---|---|---|
| 50% | 189 | −213 | 0 | 0 | 216 | 0 | −26.8 | 2.4 | 0.085 |
| 87% | 142 | −113 | 8.8 | 10.4 | 82.8 | 8.8 | 40.0 | −2.8 | 0.034 |
| 100% | 50 | −52.8 | 0.4 | 1.2 | 51.6 | 0 | −3.8 | 0.4 | 0.000 |
| 100% | 0 | 0 | 10.8 | −11.6 | −6.4 | 7.2 | 7.2 | 0 | 0.000 |

$^a$Change in the mmoles of OH groups from the bisaryl compound added to the reaction mixture; A is 2,4-dimethylphenoxide.

TABLE 11

Distribution [% Phosphorus (% P)] of Phosphorus Species, as Derived from $^{31}$P NMR Measurements, During Bisaryl Addition to Phosphorochloridite for the Synthesis of Diphosphite Ia Under Concentrated Conditions (0.35 M Phosphorochloridite Starting Concentration).

| | PCl$_3$ (% P) | APCl$_2$ (% P) | A$_2$PCl (% P) | Cyclophosphite (% P) | Monophosphite (% P) | Diphosphite (% P) | Triphosphite (% P) | POP (% P) | H (% P) | % Bisaryl Added$^a$ | A$_2$PCl (M)$^b$ |
|---|---|---|---|---|---|---|---|---|---|---|---|
| A$_2$PCl Solution | 0 | 0 | 93 | 0 | 0 | 0 | 7 | 0 | 0 | 0 | 0.350 |
| Equiv. OH Added$^c$ | | | | | | | | | | | |
| 0.150 | 0 | 0 | 70 | 0.0 | 0.0 | 17 | 7 | 2 | 4 | 16 | 0.271 |
| 0.300 | 0 | 0 | 54 | 0.0 | 0.0 | 32 | 7 | 3 | 3 | 32 | 0.203 |
| 0.460 | 0 | 0 | 34 | 0.0 | 0.0 | 52 | 7 | 3 | 4 | 49 | 0.131 |
| 0.599 | 0 | 0 | 16 | 1.0 | 0.0 | 66 | 8 | 5 | 4 | 64 | 0.077 |
| 0.761 | 0 | 0 | 0.0 | 4.0 | 0.0 | 79 | 11 | 2 | 4 | 82 | 0.018 |
| 0.761 | 0 | 0 | 0.0 | 3.0 | 0.0 | 81 | 10 | 1 | 4 | 82 | 0.015 |
| 0.761 | 0 | 0 | 0.0 | 2.0 | 0.0 | 82 | 10 | 1 | 4 | 82 | 0.015 |

TABLE 11-continued

Distribution [% Phosphorus (% P)] of Phosphorus Species, as Derived from $^{31}$P NMR Measurements, During Bisaryl Addition to Phosphorochloridite for the Synthesis of Diphosphite Ia Under Concentrated Conditions (0.35 M Phosphorochloridite Starting Concentration).

| $PCl_3$ (% P) | $APCl_2$ (% P) | $A_2PCl$ (% P) | Cyclophosphite (% P) | Monophosphite (% P) | Diphosphite (% P) | Triphosphite (% P) | POP (% P) | H (% P) | % Bisaryl Added[a] | $A_2PCl$ (M)[b] |
|---|---|---|---|---|---|---|---|---|---|---|
| 0.821 | 0 | 0 | 0.0 | 2.4 | 0.7 | 83 | 10 | 1 | 3 | 88 | 0.000 |
| 0.821 | 0 | 0 | 0.0 | 3.0 | 0.0 | 83 | 10 | 1 | 3 | 88 | 0.000 |
| 0.846 | 0 | 0 | 0.0 | 3.0 | 0.0 | 83 | 10 | 1 | 2 | 91 | 0.000 |

[a]Mole percent of total bisaryl compound IIIa added to the reaction mixture;
[b]Measured $A_2PCl$ molar concentration within the reaction mixture by $^{31}$P NMR;
[c]Molar equivalents of OH groups from the bisaryl compound IIIa added to the reaction mixture relative to total moles of phosphorochloridite, $A_2PCl$, charged to the reaction flask; A is 2,4-dimethylphenoxide.

TABLE 12

Mass Balance for the Addition of Bisaryl to Phosphorochloridite for the Synthesis of Diphosphite Ia Under Concentrated Conditions (0.35 M Phosphorochloridite Starting Concentration) as Derived from $^{31}$P NMR Measurements.

| Bisaryl Added Equiv. of Theory | OH Added[a] [mmol] | $A_2PCl$[b] [mmol] | $A_2PCl$[b] Corrected | Cyclophosphite [mmol] | Monophosphite [mmol] | Diphosphite [mmol] | Triphosphite [mmol] | Bisaryl in vs out [mmol] | $A_2PCl$[b] Conv. | $A_2PCl$[b] Conv. Corrected |
|---|---|---|---|---|---|---|---|---|---|---|
| 0% | 0 | 372 | 360 | 0 | 0 | 0 | 28 | 0.0 | 0% | 0% |
| 16% | 60 | 305 | 293 | 0 | 0 | 68 | 28 | -7.9 | 22% | 23% |
| 32% | 120 | 240 | 228 | 0 | 0 | 128 | 28 | -8.1 | 42% | 43% |
| 49% | 184 | 164 | 152 | 0 | 0 | 208 | 28 | -24.0 | 62% | 64% |
| 64% | 240 | 100 | 88 | 4 | 0 | 264 | 32 | -28.3 | 78% | 80% |
| 82% | 305 | 24 | 12 | 16 | 0 | 316 | 44 | -27.5 | 95% | 97% |
| 82% | 305 | 20 | 8 | 12 | 0 | 324 | 40 | -31.5 | 96% | 98% |
| 82% | 305 | 20 | 8 | 8 | 0 | 328 | 40 | -31.5 | 96% | 98% |
| 88% | 329 | 16 | 4 | 9.6 | 2.8 | 332 | 40 | -15.9 | 97% | 99% |
| 88% | 329 | 16 | 4 | 12 | 0 | 332 | 40 | -15.9 | 97% | 99% |
| 91% | 339 | 12 | 0 | 12 | 0 | 332 | 40 | -5.5 | 98% | 100% |

[a]Total mmoles of OH groups from the bisaryl compound added to the reaction mixture;
[b]A is 2,4-dimethylphenoxide.

TABLE 13

Differential Conversion of Phosphorus Species During Bisaryl Addition for the Synthesis of Diphosphite Under Concentrated Conditions as Derived from $^{31}$P NMR Measurements. In the Table, Δ Indicates Change From the Previous Entry.

| Bisaryl Added Equiv. | OH Added[a] Δ [mmol] | $A_2PCl$ Δ [mmol] | Cyclophosphite Δ [mmol] | Monophosphite Δ [mmol] | Diphosphite Δ [mmol] | Triphosphite Δ [mmol] | Bisaryl Balance [mmol] | P Balance [mmol] | $A_2PCl$ Conc. (M) |
|---|---|---|---|---|---|---|---|---|---|
| 16% | 60.1 | -66.8 | 0 | 0 | 68 | 0 | -7.9 | 1.2 | 0.261 |
| 32% | 59.8 | -64.8 | 0 | 0 | 60 | 0 | -0.2 | -4.8 | 0.193 |
| 49% | 64.1 | -76.4 | 0 | 0 | 80 | 0 | -15.9 | 3.6 | 0.122 |
| 64% | 55.7 | -64 | 4 | 0 | 56 | 4 | -4.3 | 0 | 0.067 |
| 82% | 64.8 | -76 | 12 | 0 | 52 | 12 | 0.8 | 0 | 0.009 |
| 82% | 0 | -4 | -4 | 0 | 8 | -4 | -4 | 0 | 0.006 |
| 82% | 0 | 0 | -4 | 0 | 4 | 0 | 0 | 0 | 0.006 |
| 88% | 24 | -4 | 1.6 | 2.8 | 4 | 0 | 15.6 | 0 | 0.003 |
| 88% | 0 | 0 | 2.4 | -2.8 | 0 | 0 | 0.4 | 0 | 0.003 |
| 91% | 10 | -4 | 0 | 0 | 0 | 0 | 10 | 0 | 0.000 |

[a]Change in the mmoles of OH groups from the bisaryl compound added to the reaction mixture; A is 2,4-dimethylphenoxide.

TABLE 14

Cyclophosphite Distribution as % Phosphorus Under Different Bisaryl Addition Conditions in Diphosphite Synthesis.

| Example | Mixing Rate (rpm) | Temperature (° C.) | $NEt_3$ Equivalents* | Bisaryl Feed Rate (equiv./hour) | Cyclophosphite Distribution (% P) |
|---|---|---|---|---|---|
| 17 | 240 | -20 | 0.89 | 15 | 12.9 |
| 18 | 240 | -20 | 1.02 | 15 | 6.7 |
| 19 | 240 | -20 | 1.14 | 15 | 7.2 |
| 20 | 470 | +20 | 1.14 | 15 | 7.8 |
| 21 | 470 | -20 | 1.14 | 15 | 1.7 |

TABLE 14-continued

Cyclophosphite Distribution as % Phosphorus Under Different Bisaryl Addition Conditions in Diphosphite Synthesis.

| Example | Mixing Rate (rpm) | Temperature (° C.) | NEt₃ Equivalents* | Bisaryl Feed Rate (equiv./hour) | Cyclophosphite Distribution (% P) |
|---|---|---|---|---|---|
| 22 | 470 | +20 | 1.34 | 5 | 2.0 |
| 23 | 470 | +20 | 1.02 | 5 | 7.4 |
| 24 | 470 | +20 | 0.87 | 15 | 19.7 |
| 25 | 470 | −20 | 1.37 | 15 | 7.4 |

*Triethylamine (NEt₃) equivalents given as mole NEt₃ per total moles of the phosphorochloridite, A₂PCl, undergoing the contacting.

TABLE 15

Distribution [% Phosphorus (% P)] of Phosphorus Species, as Derived from $^{31}$P NMR Measurements, For the More Sterically Hindered Diphosphite Ib Under Different Addition Conditions For the Bisaryl Compound.

| Example | Sample | NEt₃ Equiv.* | Bisaryl Addition Rate (Equiv./Hr) | IIb (% P) | Cyclophosphite (% P) | Monophosphite (% P) | Diphosphite (% P) | Triphosphite (% P) | POP (% P) | H (% P) |
|---|---|---|---|---|---|---|---|---|---|---|
| 26 | Before Bisaryl Addition | 1.34 | 1.4 | 91.6 | 0 | 0 | 0 | 5.7 | 0.8 | 1.3 |
| | After Bisaryl Addition | | | 1.7 | 2.5 | 4.3 | 74.2 | 14.4 | 0 | 1.9 |
| | After Stirring Over Weekend | | | 0 | 5.7 | 0 | 77.5 | 14.8 | 0 | 2.0 |
| | After Brine Wash | | | 0 | 6.0 | 0 | 81.3 | 12.7 | 0 | 0 |
| 27 | Before Bisaryl Addition | 1.37 | 5.6 | 91.7 | 0 | 0 | 0 | 5.1 | 1.4 | 0 |
| | After Bisaryl Addition | | | 10.0 | 5.2 | 1.0 | 71.0 | 12.4 | 0 | 0.4 |
| | After Stirring 3 Hours | | | 1.5 | 3.7 | 0 | 83.0 | 10.2 | 0.8 | 0.9 |
| | After Brine Wash | | | 0 | 4.1 | 0 | 84.0 | 9.5 | 0.5 | 2.0 |
| 28 | Before Bisaryl Addition | 1.38 | 0.15 | 89.5 | 0 | 0 | 0 | 5.6 | 2.5 | 2.4 |
| | After Bisaryl Addition | | | 3.2 | 4.4 | 1.0 | 77.7 | 12.1 | 0.7 | 0.9 |
| | After Stirring Over Weekend | | | 0 | 2.9 | 0 | 83.4 | 10.3 | 1.4 | 2.1 |
| | After Brine Wash | | | 0 | 2.8 | 0 | 85.5 | 9.7 | 1.1 | 0.9 |
| 29 | Before Bisaryl Addition | 1.38 | 1.5 | 93.2 | 0 | 0 | 0 | 6.2 | 0 | 0 |
| | After Bisaryl Addition | | | 1.5 | 9.0 | 2.9 | 67.1 | 17.5 | 0.7 | 1.3 |
| | After Stirring 1.5 hours | | | 0 | 5.9 | 1.1 | 80.0 | 11.7 | 0 | 1.3 |
| | After Brine Wash | | | 0 | 7.2 | 0.3 | 79.7 | 11.8 | 0.3 | 0.7 |

The $^{31}$P resonances of the individual cyclophosphites were not resolved and are reported as a summed total in Table 15; the $^{31}$P resonances of the individual triphosphites were not resolved and are reported as a summed total in the Table 15.
*Triethylamine (NEt₃) relative to total phosphorochloridite IIb charged; Examples 26 and 27 were performed with 270 rpm mixing rate and −20° C. temperature during the addition of the bisaryl compound; Examples 28 and 29 were performed with 480 rpm mixing rate and +20° C. temperature during the addition of the bisaryl compound.

TABLE 16

Distribution [% Phosphorus (% P)] of Phosphorus Species, as Derived from $^{31}$P NMR Measurements, for the Synthesis of Diphosphite Ia in the Presence of Hydrolysis Products Produced by Deliberate Addition of Water Before the Addition of the Bisaryl Compound.

| Sample Taken After | PCl₃ (% P) | APCl₂ (% P) | A₂PCl (% P) | Cyclophosphite (% P) | Monophosphite (% P) | Diphosphite (% P) | Triphosphite (% P) | POP (% P) | H (% P) | % Total Hydrolysis | Equiv. water (mmol) | Equiv. water (ppm) |
|---|---|---|---|---|---|---|---|---|---|---|---|---|
| APCl₂ generated | 5.5 | 91.9 | 2.6 | 0.0 | 0.0 | 0.0 | 0.0 | 0.0 | 0.0 | 0.0 | 0.0 | 0 |
| A₂PCl generated | 0.0 | 1.8 | 94.9 | 0.0 | 0.0 | 0.0 | 0.6 | 0.0 | 2.7 | 2.7 | 5.4 | 135 |
| H₂O added | 0.0 | 1.4 | 78.1 | 0.0 | 0.0 | 0.0 | 4.9 | 0.0 | 15.6 | 15.6 | 31.1 | 778 |
| NEt₃ added | 0.0 | 0.0 | 72.6 | 0.0 | 0.0 | 0.0 | 5.4 | 18.9 | 3.1 | 12.6 | 25.2 | 630 |
| 40 g bisaryl added | 0.0 | 0.0 | 20.1 | 0.6 | 0.0 | 43.5 | 7.7 | 25.1 | 3.1 | 15.6 | 31.2 | 781 |

TABLE 16-continued

Distribution [% Phosphorus (% P)] of Phosphorus Species, as Derived from $^{31}$P NMR Measurements, for the Synthesis of Diphosphite Ia in the Presence of Hydrolysis Products Produced by Deliberate Addition of Water Before the Addition of the Bisaryl Compound.

| Sample Taken After | $PCl_3$ (% P) | $APCl_2$ (% P) | $A_2PCl$ (% P) | Cyclophosphite (% P) | Monophosphite (% P) | Diphosphite (% P) | Triphosphite (% P) | POP (% P) | H (% P) | % Total Hydrolysis | Equiv. water (mmol) | Equiv. water (ppm) |
|---|---|---|---|---|---|---|---|---|---|---|---|---|
| 20 g bisaryl added | 0.0 | 0.0 | 3.5 | 0.9 | 0.0 | 59.0 | 8.1 | 26.3 | 2.2 | 15.4 | 30.8 | 769 |
| 16 Hours | 0.0 | 0.0 | 0.0 | 0.9 | 0.0 | 62.4 | 8.6 | 24.5 | 3.6 | 15.8 | 31.7 | 792 |
| 5 g more bisaryl added | 0.0 | 0.0 | 0.0 | 1.6 | 0.5 | 65.3 | 9.0 | 22.3 | 1.3 | 12.5 | 24.9 | 623 |

TABLE 17

Distribution [% Phosphorus (% P)] of Phosphorus Species, as Derived from $^{31}$P NMR Measurements, for the Synthesis of Diphosphite Ia in the Presence of Hydrolysis Products Produced by Deliberate Addition of Water Before the Addition of the Bisaryl Compound.

| Sample Taken After | $PCl_3$ (% P) | $APCl_2$ (% P) | $A_2PCl$ (% P) | Cyclophosphite (% P) | Monophosphite (% P) | Diphosphite (% P) | Triphosphite (% P) | POP (% P) | H (% P) | % Total Hydrolysis | Equiv. water (mmol) | Equiv. water (ppm) |
|---|---|---|---|---|---|---|---|---|---|---|---|---|
| $APCl_2$ generated | 3.3 | 92.0 | 2.5 | 0.0 | 0.0 | 0.0 | 0.0 | 0.0 | 2.2 | 2.2 | 4.4 | 110 |
| $A_2PCl$ generated | 0.0 | 2.6 | 92.5 | 0.0 | 0.0 | 0.0 | 4.1 | 0.0 | 0.9 | 0.9 | 1.7 | 44 |
| $NEt_3$ added | 0.0 | 1.8 | 88.6 | 0.0 | 0.0 | 0.0 | 6.6 | 0.0 | 2.9 | 2.9 | 5.8 | 146 |
| 40 g bisaryl/ $H_2O$ added | 0.0 | 0.0 | 37.8 | 3.3 | 0.0 | 37.1 | 9.0 | 6.1 | 6.7 | 9.7 | 19.4 | 485 |
| 20 g bisaryl added | 0.0 | 0.0 | 4.8 | 5.0 | 2.0 | 52.4 | 12.3 | 19.2 | 4.3 | 13.9 | 27.8 | 694 |
| 16 hours | 0.0 | 0.0 | 0.0 | 7.0 | 2.2 | 54.4 | 12.4 | 20.2 | 3.7 | 13.8 | 27.7 | 691 |
| 5 g bisaryl added | 0.0 | 0.0 | 0.0 | 9.9 | 0.0 | 56.0 | 12.3 | 19.1 | 2.7 | 12.3 | 24.6 | 614 |

TABLE 18

Distribution [% Phosphorus (% P)] of Phosphorus Species, as Derived from $^{31}$P NMR Measurements, of Phosphorus-Containing Acidic Compounds and Cyclophosphite in the Synthesis of Diphosphite Ia With 2 M Feeds at Different Levels of Triethylamine and Acidic Hydrolysis Products (H) Active in the Catalytic Conversion of the Monophosphite Intermediate to Cyclophosphite.

| Example | Bisaryl Addition Rate (Equiv./Hour) | $NEt_3$ Equivalents$^c$ | H (% P) | Cyclophosphite (% P) |
|---|---|---|---|---|
| 30 | Portions$^b$ | 1.4 | 1.3-3.6 | 1.6 |
| 31 | Portions$^b$ | 1.4 | 2.7-6.7 | 9.9 |
| 21 | 15 | 1.135 | <1 | 3.8 |
| 22$^a$ | 5 | 1.344 | 0 | 2.0 |
| 23 | 5 | 1.016 | 0.6-1.2 | 7.4 |
| 24 | 15 | 0.873 | 1.9-3.3 | 19.7 |
| 25 | 15 | 1.37 | 0.9-2.6 | 7.4 |

$^a$2000 mL scale;
$^b$Bisaryl compound was added in portions versus a continuous addition rate in the other Examples in this Table;
$^c$Triethylamine ($NEt_3$) relative to total phosphorochloridite IIa charged.

TABLE 19

Distribution [% Phosphorus (% P)] of Phosphorus Species, as Derived from $^{31}$P NMR Measurements, in the Synthesis of Diphosphite Ia at Different Concentrations, Levels of Triethylamine, and Acidic Hydrolysis Products, as Derived from $^{31}$P NMR Measurements.

| Example | Relative Conc. | Cyclophosphite (% P) | Monophosphite (% P) | Diphosphite (% P) | Triphosphite (% P) | POP (% P) | H (% P) | Equiv. Water after $Et_3N$ Addition (ppm) | Equiv. Water after Bisaryl Addition (ppm) | Equiv. Water at End (ppm) |
|---|---|---|---|---|---|---|---|---|---|---|
| 30 | 1 | 1.6 | 0.5 | 65.3 | 9.0 | 22.3 | 1.3-3.6 | 778 | 792 | 623 |
| 31* | 1 | 9.9 | 0.0 | 56.0 | 12.3 | 19.1 | 2.7-6.7 | 146 | 694 | 614 |

TABLE 19-continued

Distribution [% Phosphorus (% P)] of Phosphorus Species, as Derived from $^{31}$P NMR Measurements, in the Synthesis of Diphosphite
Ia at Different Concentrations, Levels of Triethylamine, and Acidic Hydrolysis Products, as Derived from $^{31}$P NMR Measurements.

| Example | Relative Conc. | Cyclophosphite (% P) | Monophosphite (% P) | Diphosphite (% P) | Triphosphite (% P) | POP (% P) | H (% P) | Equiv. Water after Et$_3$N Addition (ppm) | Equiv. Water after Bisaryl Addition (ppm) | Equiv. Water at End (ppm) |
|---|---|---|---|---|---|---|---|---|---|---|
| 32A | ⅓ | 11.1 | 2.9 | 12.5 | 20.9 | 40.3 | 2-16 | 608 | 913 | 813 |
| 32B | 1 | 2.4 | 0.5 | 50.8 | 12.5 | 31.4 | 1.7-5.6 | 975 | 1003 | 869 |

*Example 31 final results; For all these Examples, the stirring rate was 480 rpm, the temperature was 20° C., all the triethylamine (1.4 molar equivalents of triethylamine per molar equivalent of total phosphorochloridite charged) was added before the bisaryl compound was added in portions; For Example 30, 30 mmol water was added before NEt$_3$; For Example 31, 30 mmol water added with the bisaryl compound.

TABLE 20

Distribution [% Phosphorus (% P)] of Phosphorus Species, as Derived from $^{31}$P NMR Measurements, in the
Synthesis of Diphosphite Ia under Dilute Concentrations (Example 32A), as Derived from $^{31}$P NMR Measurements.

| Sample Taken After | APCl$_2$ (% P) | A$_2$PCl (% P) | Cyclophosphite (% P) | Monophosphite (% P) | Diphosphite (% P) | Triphosphite (% P) | POP (% P) | H (% P) | H$_2$O (Mol %) | H$_2$O (mmol) | H$_2$O (ppm) | H Conc. (mmol/Kg) |
|---|---|---|---|---|---|---|---|---|---|---|---|---|
| A$_2$PCl | 1.8 | 88.1 | 0.0 | 0.0 | 0.0 | 7.2 | 0.0 | 2.9 | 2.9 | 5.7 | 36 | 2 |
| Separate | 1.6 | 81.3 | 0.0 | 0.0 | 0.0 | 7.2 | 0.0 | 9.9 | 9.9 | 5.0 | 124 | 7 |
| Dilute | 1.0 | 71.5 | 0.0 | 0.0 | 0.0 | 6.8 | 0.0 | 20.7 | 20.7 | 10.3 | 259 | 14 |
| NEt$_3$ | 0.0 | 45.3 | 0.0 | 0.0 | 0.0 | 8.1 | 44.6 | 2.0 | 24.3 | 12.2 | 304 | 1 |
| Bisaryl | 0.0 | 0.0 | 10.7 | 0.0 | 11.9 | 20.8 | 40.4 | 16.4 | 36.5 | 18.3 | 457 | 11 |
| +2 hours | 0.0 | 0.0 | 11.1 | 2.9 | 12.5 | 20.9 | 40.3 | 12.4 | 32.5 | 16.3 | 407 | 9 |

TABLE 21

Distribution [% Phosphorus (% P)] of Phosphorus Species, as Derived
from $^{31}$P NMR Measurements, in the Synthesis of Diphosphite Ia (Example 32B).

| Sample Taken After | APCl$_2$ (% P) | A$_2$PCl (% P) | Cyclophosphite (% P) | Monophosphite (% P) | Diphosphite (% P) | Triphosphite (% P) | POP (% P) | H (% P) | H$_2$O (Mol %) | H$_2$O (mmol) | H$_2$O (ppm) | H Conc. (mmol/Kg) |
|---|---|---|---|---|---|---|---|---|---|---|---|---|
| Separate | 1.6 | 81.3 | 0.0 | 0.0 | 0.0 | 7.2 | 0.0 | 9.9 | 9.9 | 5.0 | 124 | 7 |
| Transfer | 1.7 | 72.3 | 7.3 | 0.0 | 0.0 | 0.0 | 0.0 | 18.8 | 18.8 | 28.2 | 939 | 52 |
| NEt$_3$ | 0.0 | 55.5 | 0.0 | 0.0 | 0.0 | 8.1 | 32.2 | 4.2 | 20.4 | 30.5 | 1018 | 12 |
| ⅔ Bisaryl | 0.0 | 8.3 | 1.2 | 0.0 | 48.0 | 9.5 | 30.0 | 3.0 | 18.0 | 27.1 | 902 | 8 |
| ⅓ Bisaryl | 0.0 | 0.0 | 1.9 | 0.0 | 51.5 | 11.1 | 32.1 | 3.5 | 19.5 | 29.3 | 975 | 10 |
| +16 hours | 0.0 | 0.0 | 2.4 | 0.9 | 49.8 | 11.5 | 32.6 | 2.8 | 19.1 | 28.6 | 953 | 8 |

TABLE 22

Distribution [% Phosphorus (% P)] of Phosphorus Species, as Derived from
$^{31}$P NMR Measurements, in the Synthesis of Diphosphite Under Dilute Conditions at 20° C.

| Example | Bisaryl addition rate (equiv./hour) | Cyclophosphite (% P) | Monophosphite (% P) | Diphosphite (% P) | Triphosphite (% P) | POP (% P) | H (% P) | Equiv. Water after Et$_3$N Addition (ppm) | Equiv. Water after Bisaryl Addition (ppm) | Equiv. Water at End (ppm) |
|---|---|---|---|---|---|---|---|---|---|---|
| 34[a,c] | 5.1 | 25.5 | 0.0 | 45.3 | 20.6 | 3.4 | 5.1 | 120 | 171 | 77 |
| 35[a,c] | 5 | 29.2 | 0.0 | 35.7 | 32.0 | 1.4 | 2.6 | 112 | 116 | 35 |
| 36[b,c] | 0.23 | 19.9 | 0.0 | 53.8 | 20.7 | 4.5 | 1.1 | 49 | 154 | 49 |
| 37[b,d] | portions | 7.9 | 0.0 | 51.3 | 21.0 | 9.5 | 10.4 | 257 | 559 | 223 |
| 38[b,c,e] | portions | 6.0 | 0.0 | 70.0 | 16.0 | 6.6 | 1.5 | 159 | 272 | 84 |
| 39[b,d,f] | portions | 5.2 | 0.0 | 61.2 | 11.3 | 20.2 | 2.1 | 288 | 288 | 180 |

All Examples of Table 22 were performed at reactant concentrations of one quarter those of Example 32B;
[a]270 rpm stirring rate;
[b]480 rpm stirring rate;
[c]1.35 molar equivalents of NEt$_3$ per mole phosphorochloridite charged to the reactor;
[d]1.45 molar equivalents of NEt$_3$ per mole phosphorochloridite charged to the reactor;
[e]feed solutions (NEt$_3$ and bisaryl compound) dried by contact with dried molecular sieves;
[f]same as Example 38 but additional NEt$_3$ was added to the reaction mixture at the end.

TABLE 23

Distribution [% Phosphorus (% P)] of Phosphorus Species, as Derived from $^{31}$P NMR Measurements, for the Reaction of PCl$_3$ with 2,4-Xylenol to Form a Phosphorochloridite Mixture and the Subsequent Reaction at 55° C. of the Phosphorochloridite Mixture with the Bisaryl Compound and Triethylamine.

| | PCl$_3$ (% P) | APCl$_2$ (% P) | A$_2$PCl (% P) | Cyclophosphite (% P) | Monophosphite (% P) | Diphosphite (% P) | Triphosphite (% P) | POP (% P) | H (% P) |
|---|---|---|---|---|---|---|---|---|---|
| Molar Equivalent 2,4-Xylenol Added | | | | | | | | | |
| 1.0 | 3 | 91 | 5 | 0 | 0 | 0 | 0 | | |
| 2.0 | 0 | 2 | 89 | 0 | 0 | 0 | 8 | | |
| % Feed Bisaryl Added | | | | | | | | | |
| 50% | | 0 | 46.5 | 2.1 | | 36.9 | 9.6 | 0.9 | |
| 75% | | | 23.8 | 2.5 | | 56.6 | 10.3 | 1.1 | |
| 100% | | | 3.3 | 3.2 | 2.4 | 72.5 | 11.6 | 1.1 | 0.1 |
| 100% | | | 0.6 | 3.0 | 0 | 76.5 | 12.3 | 0.7 | 0.2 |

TABLE 24

Distribution [% Phosphorus (% P)] of Phosphorus Species, as Derived from $^{31}$P NMR Measurements, for the Reaction of PCl$_3$ with 2,4-Xylenol to Form a Phosphorochloridite Mixture and the Subsequent Reaction at 35° C. of the Phosphorochloridite Mixture with the Bisaryl Compound and Triethylamine.

| | PCl$_3$ (% P) | APCl$_2$ (% P) | A$_2$PCl (% P) | Cyclophosphite (% P) | Monophosphite (% P) | Diphosphite (% P) | Triphosphite (% P) | POP (% P) | H (% P) |
|---|---|---|---|---|---|---|---|---|---|
| Molar Equivalent 2,4-Xylenol Added | | | | | | | | | |
| 1.0 | 7 | 89 | 4 | 0 | 0 | 0 | | | |
| 2.0 | 0 | 1 | 89 | 0 | 0 | 0 | 9 | | |
| % Feed Bisaryl Added | | | | | | | | | |
| 50% | | 0 | 44.7 | 1.2 | 0.0 | 39.6 | 9.7 | 0.5 | 44.7 |
| 75% | | | 22.6 | 1.5 | | 57.8 | 10.2 | 0.9 | 22.6 |
| 100% | | | 2.4 | 2.7 | 2.2 | 73.0 | 11.5 | 0.6 | 2.4 |
| 100% | | | 0.9 | 2.8 | 0.8 | 76.1 | 11.6 | 0.6 | 0.9 |

TABLE 25

Distribution [% Phosphorus (% P)] of Phosphorus Species, as Derived from $^{31}$P NMR Measurements, for the Reaction of PCl$_3$ with 2,4-Xylenol to Form a Phosphorochloridite Mixture and the Subsequent Reaction at 15° C. of the Phosphorochloridite Mixture with the Bisaryl Compound and Triethylamine.

| | PCl$_3$ (% P) | APCl$_2$ (% P) | A$_2$PCl (% P) | Cyclophosphite (% P) | Monophosphite (% P) | Diphosphite (% P) | Triphosphite (% P) | POP (% P) | H (% P) |
|---|---|---|---|---|---|---|---|---|---|
| Molar Equivalent 2,4-Xylenol Added | | | | | | | | | |
| 2.0 | 0 | 2 | 87 | 0 | 0 | 0 | 8 | | |
| % Feed Bisaryl Added | | | | | | | | | |
| 60% | | 0 | 34.9 | 1.8 | 0.2 | 46.8 | 11.4 | 0.7 | |
| 100% | | | 0.8 | 3.0 | 3.3 | 73.5 | 12.5 | 0.4 | |

TABLE 26

Distribution [% Phosphorus (% P)] of Phosphorus Species, as Derived from $^{31}$P NMR Measurements, for the Reaction of PCl$_3$ with 2,4-Xylenol to Form a Phosphorochloridite Mixture and the Subsequent Reaction at 10° C. of the Phosphorochloridite Mixture with the Bisaryl Compound and Triethylamine.

| | PCl$_3$ (% P) | APCl$_2$ (% P) | A$_2$PCl (% P) | Cyclophosphite (% P) | Monophosphite (% P) | Diphosphite (% P) | Triphosphite (% P) | POP (% P) | H (% P) |
|---|---|---|---|---|---|---|---|---|---|
| Molar Equivalent 2,4-Xylenol Added | | | | | | | | | |
| 1.0 | 4 | 88 | 7 | 0 | 0 | 0 | | | |
| 2.0 | | 4 | 85 | 0 | 0 | 0 | 11 | | |
| % Feed Bisaryl Added | | | | | | | | | |
| 50% | | 0 | 49.5 | 3.2 | 0 | 30.2 | 11.9 | 0.7 | |
| 100% | | | 0.4 | 4.4 | 2.8 | 71.1 | 13.4 | 0.4 | |

What is claimed is:

1. A method for producing a diphosphite of Structure I,

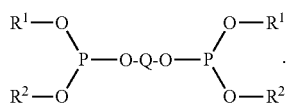

Structure I comprising the steps of:
contacting a phosphorochloridite of Structure II,

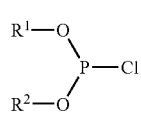

Structure II with a bisaryl compound selected from the group consisting of Structure III, Structure IV, and Structure V,

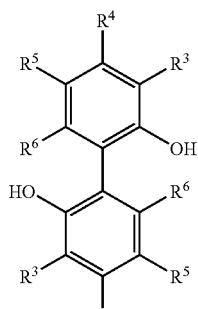

Structure III

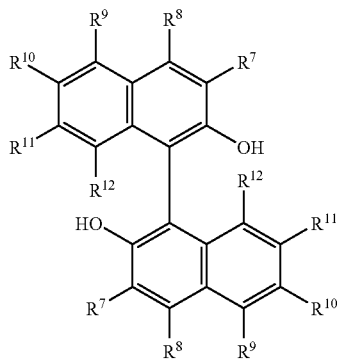

Structure IV

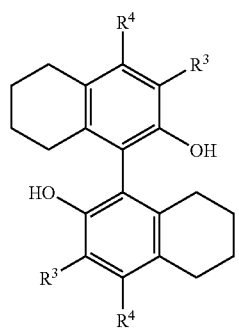

Structure V and a tertiary organic amine, comprising a basic nitrogen atom or a plurality of nitrogen atoms, to produce a reaction mixture comprising a diphosphite of Structure I;
wherein,
the contacting step is carried out by at least one contacting method selected from the group consisting of,
(i). feeding the bisaryl compound to a mixture of phosphorochloridite and tertiary organic amine, and
(ii). feeding the bisaryl compound and the tertiary organic amine either separately or as a mixture to the phosphorochloridite;
and the contacting step is carried out by controlling the feeding such that:
a first mole ratio is maintained at equal to or greater than 2.0 during at least an initial stage and a final stage of the contacting step, wherein the first mole ratio is defined as moles of phosphorochloridite in the reaction mixture divided by moles of bisaryl compound fed to the reaction mixture, and
a second mole ratio is at least 1.0 during the contacting step, wherein the second mole ratio is defined as moles of basic nitrogen atoms from the tertiary organic amine fed to the reaction mixture divided by moles of phosphorochloridite in the reaction mixture; and
the method is characterized in that the contacting occurs at a temperature from about 15° C. to about 110° C. to produce the diphosphite in the reaction mixture with a selectivity between 70% and 100% from the bisaryl compound;
wherein,
the selectivity equals moles of diphosphite produced in the reaction mixture divided by total moles of the bisaryl compound contacting the phosphorochloridite;

wherein in Structures I to V,

R$^1$ and R$^2$ are the same or different, substituted or unsubstituted, monovalent aryl groups; each of R$^3$, R$^4$, R$^5$, R$^6$, R$^7$, R$^8$, R$^9$, R$^{10}$, R$^{11}$ and R$^{12}$ is independently selected from the group consisting of hydrogen, alkyl, aryl, heteroaryl, aryloxy, heteroaryloxy, alkyloxy, alkoxyalkyl, acetal, carboaryloxy, carboalkoxy, arylcarbonyl, alkylcarbonyl, oxazole, amine, amide, nitrile, mercaptyl, and halogenyl groups; and $^-$O-Q-O$^-$ is a dianion of the bisaryl compound.

2. The method of claim 1 wherein the reaction mixture further comprises at least one aromatic hydrocarbon solvent.

3. The method of claim 1 further comprising controlling the feeding such that the first mole ratio is between 2.1 to 2.7 during the stage of the contacting step wherein phosphorochloridite conversion is between 90% and 100%.

4. The method of claim 1 further comprising controlling the feeding such that a phosphorochloridite concentration is greater than or equal to 0.02 moles per liter in the reaction mixture during the stage of the contacting step wherein phosphorochloridite conversion is from 0% to 90%.

5. The method of claim 4 wherein the phosphorochloridite concentration is between 0.02 and 2.0 moles per liter in the reaction mixture during the stage of the contacting step wherein phosphorochloridite conversion is from 0% to 90%.

6. The method of claim 1 further comprising controlling the second mole ratio from 1.0 to 1.5 during any stage of the contacting step.

7. The method of claim 1 further comprising feeding the bisaryl compound to the phosphorochloridite at a feed rate between 0.04 and 10 molar equivalents per hour, relative to total moles of phosphorochloridite undergoing the contacting step.

8. The method of claim 1 further comprising feeding the bisaryl compound to the phosphorochloridite as a bisaryl solution comprising the bisaryl compound and hydrocarbon solvent.

9. The method of claim 8 wherein the reaction mixture further comprises an upper liquid surface, the contacting further comprises providing a stirring shaft comprising at least one impeller attached to the stirring shaft wherein at least one impeller is located below the upper liquid surface, and the feeding further comprises providing rotational energy to the stirring shaft to mechanically stir the reaction mixture.

10. The method of claim 9 further comprising feeding the bisaryl solution to the phosphorochloridite by at least one mixing method selected from the group consisting of, feeding the bisaryl compound to the reaction mixture above the upper liquid surface by flowing the bisaryl solution through at least one liquid distributor that disperses the bisaryl solution over at least a portion of the upper liquid surface;

feeding the bisaryl compound to the reaction mixture above the upper liquid surface by flowing the bisaryl solution through at least one liquid distributor that disperses the bisaryl solution over at least a portion of the upper surface and feeding the tertiary organic amine to the reaction mixture below the upper liquid surface;

feeding the bisaryl compound to the reaction mixture by flowing the bisaryl solution through at least one feed line that directs the bisaryl solution toward an impeller located below the upper liquid surface;

feeding the bisaryl compound to the reaction mixture by flowing the bisaryl solution through at least one feed line that directs the bisaryl solution toward an impeller located below the upper liquid surface and feeding the tertiary organic amine to the reaction mixture by flowing the tertiary organic amine through at least one feed line that directs the tertiary organic amine toward an impeller located below the upper liquid surface; and the bisaryl solution further comprises at least a portion of the tertiary organic amine fed to the reaction mixture and feeding the bisaryl compound to the reaction mixture by flowing the bisaryl solution, further comprising the tertiary organic amine, through at least one feed line that directs the bisaryl solution toward an impeller located below the upper liquid surface.

11. The method of claim 1 wherein the bisaryl compound, the tertiary organic amine, or a combination of the bisaryl compound and the tertiary organic amine, contacting the phosphorochloridite further comprise a total of from 0 ppm to 300 ppm by weight of water.

12. The method of claim 1 further comprising precipitating a tertiary organic amine hydrogen chloride salt from the reaction mixture during the contacting step.

13. The method of claim 1 further comprising producing at least one phosphorus-containing co-product in the reaction mixture selected from the group consisting of P(OR$^1$)(OR$^2$)$_2$, P(OR$^1$)$_2$(OR$^2$), P(OR$^1$)$_3$, P(OR$^2$)$_3$, a compound of Structure VIa, and a compound of Structure VIb,

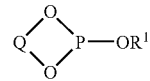

Structure VIa

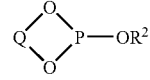

Structure VIb wherein,
less than 30% of the total phosphorus in the reaction mixture is in the form of the at least one phosphorus-containing co-product produced from the contacting.

14. The method of claim 1 wherein the first mole ratio is at least 2.0 during all of the contacting step, and the second mole ratio is at least 1.0 during all of the contacting step.

* * * * *